(12) United States Patent
MacKenzie et al.

(10) Patent No.: US 6,262,075 B1
(45) Date of Patent: *Jul. 17, 2001

(54) PIPERIDONE TACHYKININ ANTAGONISTS

(75) Inventors: Alexander Roderick MacKenzie; Allan Patrick Marchington; Donald Stuart Middleton; Sandra Dora Meadows, all of Sandwich (GB)

(73) Assignee: Pfizer Inc, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/117,011

(22) PCT Filed: Jan. 9, 1997

(86) PCT No.: PCT/EP97/00162

§ 371 Date: Jul. 20, 1998

§ 102(e) Date: Jul. 20, 1998

(87) PCT Pub. No.: WO97/27185

PCT Pub. Date: Jul. 31, 1997

(30) Foreign Application Priority Data

Jan. 22, 1996 (GB) .................................................. 9601202

(51) Int. Cl.[7] ........................ A61K 31/454; C07D 401/14
(52) U.S. Cl. ............................................ 514/316; 546/187
(58) Field of Search ............................... 514/316; 546/187

(56) References Cited

U.S. PATENT DOCUMENTS 5,968,923 * 10/1999 MacKenzie et al. ................ 514/210

FOREIGN PATENT DOCUMENTS

| 0512901A1 | 11/1992 | (EP) . |
| 0723959A1 | 7/1996 | (EP) . |
| WO 96/05193 | 2/1996 | (WO) . |

* cited by examiner

Primary Examiner—Patricia L. Morris
(74) Attorney, Agent, or Firm—Peter C. Richardson; Paul H. Ginsburg; A. David Joran

(57) ABSTRACT

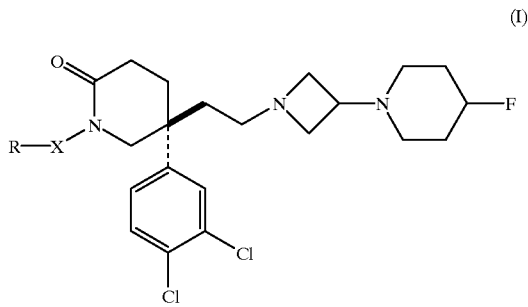

The present invention provides compounds of formula (I) and the pharmaceutically acceptable acid addition salts thereof, wherein X is a direct link or $C_1$–$C_4$ alkylene; and R is $C_3$–$C_7$ cycloalkyl optionally substituted by 1 or 2 substituents each independently selected from fluoro and $C_3$–$C_7$ cycloalkyl: with the proviso that X is not methylene when R is cyclopropyl, together with processes for the preparation of, intermediates used in the preparation of, compositions containing and uses of, such compounds. These compounds are useful as tachykinin antagonists.

17 Claims, No Drawings

PIPERIDONE TACHYKININ ANTAGONISTS

This invention relates to piperidones. More particularly, this invention relates to 5-(3,4-dichlorophenyl)-5-(2-[3-(4-fluoropiperidin-1-yl)]azetidin-1-yl)ethylpiperidin-2-one derivatives and to processes for the preparation of, intermediates used in the preparation of, compositions containing and uses of, such derivatives.

These derivatives are antagonists of tachykinins, including NKA, NKB and Substance P, acting at the human neurokinin-1 ($NK_1$), neurokinin-2 ($NK_2$) or neurokinin-3 ($NK_3$) receptor, or any combination thereof. The derivatives are therefore useful for preventing or treating an inflammatory disease such as arthritis, psoriasis, asthma or inflammatory bowel disease, a central nervous system (CNS) disorder such as anxiety, depression, dementia or psychosis, a gastro-intestinal (GI) disorder such as functional bowel disease, irritable bowel syndrome, gastro-oesophageal reflux, faecal incontinence, colitis or Crohn's disease, a disease caused by *Helicobacter pylori* or other urease-positive Gram negative bacteria, an urogenital tract disorder such as incontinence, impotence, hyperreflexia or cystitis, a pulmonary disorder such as chronic obstructive airways disease, an allergy such as eczema, contact dermatitis or rhinitis, a hypersensitivity disorder such as to poison ivy, a vasospastic disease such as angina or Reynaud's disease, a fibrosing or collagen disease such as scleroderma or eosinophillic fascioliasis, reflux sympathetic dystrophy such as shoulder/hand syndrome, an addiction disorder such as alcoholism, a stress-related somatic disorder, a peripheral neuropathy such as diabetic neuropathy, neuralgia, causalgia, painful neuropathy, a burn, herpetic neuralgia or post-herpetic neuralgia, a neuropathological disorder such as Alzheimer's disease or multiple sclerosis, a disorder related to immune enhancement or suppression such as systemic lupus erythematosis, a rheumatic disease such as fibrositis, emesis, cough, acute or chronic pain, migraine, or an opthalmic disease such as proliferative retinopathy.

These derivatives are particularly potent and selective antagonists of tachykinins, including NKA, NKB and Substance P, acting at the human $NK_2$ receptor. They are particularly useful for treating or preventing an inflammatory disease such as arthritis, psoriasis, asthma or inflammatory bowel disease, a central nervous system (CNS) disorder such as anxiety, depression, dementia or psychosis, a gastrointestinal (GI) disorder such as functional bowel disease, irritable bowel syndrome, gastro-oesophageal reflux, faecal incontinence, colitis or Crohn's disease, an urogenital tract disorder such as incontinence, hyperreflexia or cystitis, a pulmonary disorder such as chronic obstructive airways disease, an allergy such as eczema, contact dermatitis or rhinitis, a hypersensitivity disorder such as to poison ivy, a peripheral neuropathy such as diabetic neuropathy, neuralgia, causalgia, painful neuropathy, a burn, herpetic neuralgia or post-herpetic neuralgia, cough or acute or chronic pain.

International Patent Application Publication no. WO96/05193 discloses azetidinylalkyllactam derivatives with tachykinin antagonist activity, including 1-cyclopropylmethyl-5-(3,4-dichlorophenyl)-5-(2-[3-(4-fluoropiperidin-1-yl)]azetidin-1-yl)ethylpiperidin-2-one and pharmaceutically acceptable salts thereof. EP-A-0512901 discloses cyclic amine derivatives which have neurokinin receptor antagonist activity. EP-A-0723959 describes lactam derivatives which have tachykinin receptor antagonist activity.

The present invention provides a compound of the formula:-

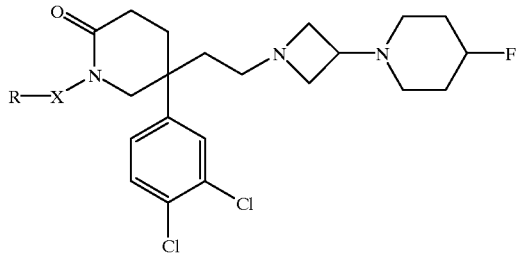

or a pharmaceutically acceptable acid addition salt thereof, wherein

X is a direct link or $C_1$–$C_4$ alkylene; and

R is $C_3$–$C_7$ cycloalkyl optionally substituted by 1 or 2 substituents each independently selected from fluoro and $C_3$–$C_7$ cycloalkyl: with the proviso that X is not methylene when R is cyclopropyl.

In the above definition of a compound of the formula (I), an alkylene group containing 3 or 4 carbon atoms may be straight- or branched-chain.

Preferably, X is a direct link, methylene or ethylene.

Most preferably, X is methylene.

Preferably, R is $C_3$–$C_6$ cycloalkyl optionally substituted by 1 or 2 substituents each independently selected from fluoro and $C_3$–$C_6$ cycloalkyl, preferably cyclopropyl.

More preferably, R is cyclopropyl, 1-cyclopropylcyclopent-1-yl, cyclohexyl or 4,4-difluorocyclohexyl.

Most preferably, R is 4,4-difluorocyclohexyl.

Suitable acid addition salts are formed from acids which form non-toxic salts and examples include the hydrochloride, hydrobromide, hydroiodide, sulphate, hydrogen sulphate, nitrate, phosphate, hydrogen phosphate, acetate, maleate, fumarate, lactate, tartrate, citrate, gluconate, succinate, benzoate, methanesulphonate, benzenesulphonate, p-toluenesulphonate, 5-sulphosalicylate and 10-camphorsulphonate salts. A preferred acid addition salt is the disuccinate salt.

For a review on suitable acid addition salts see Berge et al, J. Pharm. Sci., 66, 1–19 (1977).

A compound of the formula (I) contains at least one asymmetric carbon atom and therefore exists in two or more stereoisomeric forms. The present invention includes the individual stereoisomers of the compounds of the formula (I) and mixtures thereof.

Separation of diastereoisomers may be achieved by conventional techniques, e.g. by fractional crystallisation, chromatography or H.P.L.C. of a stereoisomeric mixture of a compound of the formula (I) or a suitable salt or derivative thereof. An individual enantiomer of a compound of the formula (I) may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid.

The preferred compounds of the formula (I) have the (S)-stereochemistry at the 5-position of attachment of the 3,4-dichlorophenyl and 2-[3-(4-fluoropiperidin-1-yl)]azetidin-1-ylethyl groups to the piperidin-2-one ring, i.e.

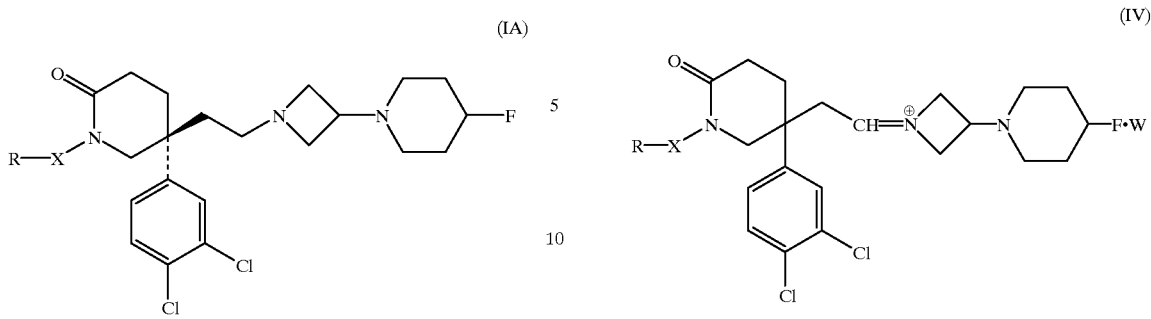

wherein X and R are as previously defined for a compound of the formula (I).

Preferred examples of a compound of the formula (I) are those wherein:

(i) R—X— is 4,4-difluorocyclohexylmethyl;
(ii) R—X— is cyclohexyl;
(iii) R—X— is 1-cyclopropylcyclopent-1-yl; or
(iv) R—X— is 2-cyclopropylethyl:

or any such compound with the (S)- stereochemistry at the 5-position of the 2-piperidinone ring, or a pharmaceutically acceptable acid addition salt of any thereof.

A particularly preferred compound of the formula (I) is 5(S)-5-(3,4-dichlorophenyl)-1-(4,4-difluorocyclohexylmethyl)-5-(2-[3-(4-fluoropiperidin-1-yl)]azetidin-1-yl)ethylpiperidin-2-one or an acid addition salt thereof and preferably a disuccinate salt thereof.

The compounds of the formula (I) provided by the invention can be prepared by the following methods:

1) The compounds of the formula (I) can be prepared by reductive amination using as starting materials a compound of the formula:

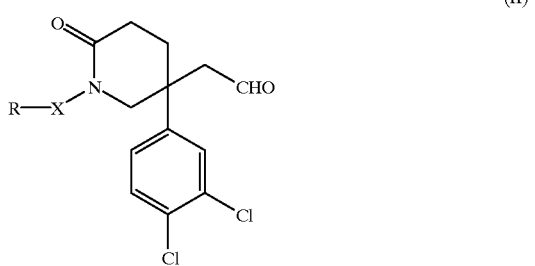

where R and X are as previously defined for a compound of the formula (I), and a compound of the formula:

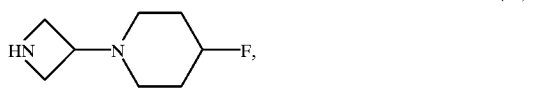

or an acid addition salt thereof. The reaction is preferably carried out in the presence of a suitable acid, e.g. acetic acid.

The reaction proceeds via the initial formation of an intermediate iminium salt of the formula:

where W is an anion (e.g. acetate) derived from a suitable acid (e.g. acetic acid), which may be stable and isolatable. The reaction is preferably carried out without isolation of the intermediate of the formula (IV), in which case it is reduced in situ to provide a compound of formula (I).

In a typical procedure, an aldehyde of the formula (II) is first reacted with an azetidine of the formula (III) in a suitable solvent, e.g. tetrahydrofuran, and the mixture is then treated with a suitable reducing agent, e.g. sodium triacetoxyborohydride or sodium cyanoborohydride, in the presence of a suitable acid, e.g. acetic acid, to give the required product. If an acid addition salt of an azetidine of the formula (III) is used as a starting material, a suitable acid acceptor, e.g. triethylamine, is preferably added prior to the addition of the reducing agent.

3-(4-Fluoropiperidin-1-yl)azetidine dihydrochloride or toluenesulphonate (tosylate) is a preferred starting material for this method.

The reaction is typically carried out at room temperature.

The compounds of the formula (III) can be prepared by conventional procedures.

The aldehydes of the formula (II) can be prepared by the method shown in Scheme 1:

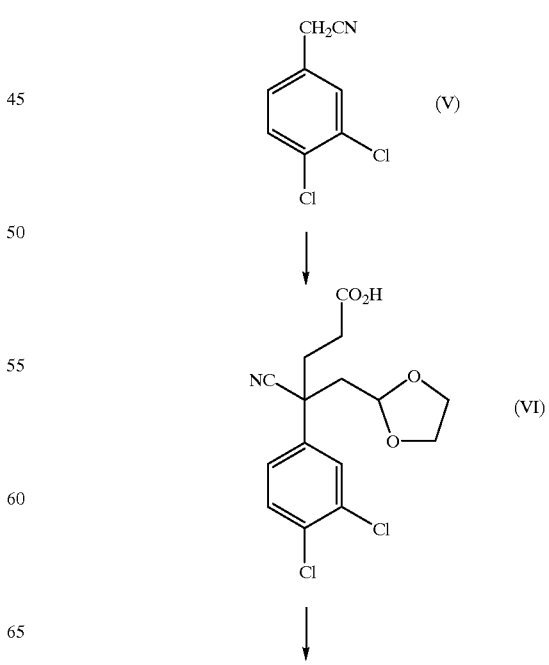

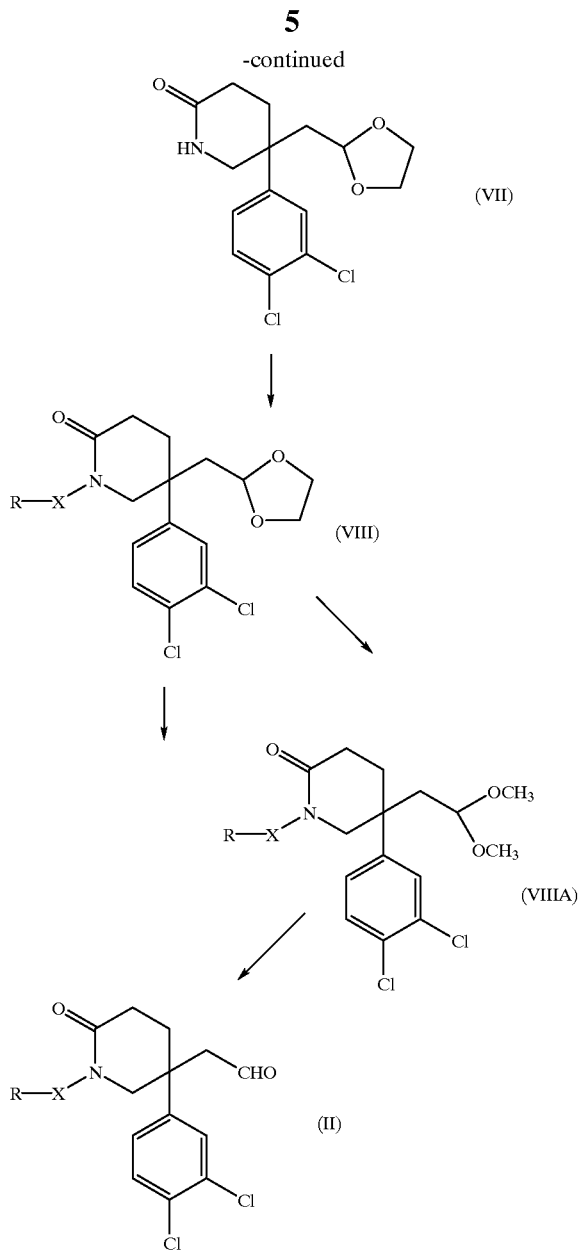

wherein R and X are as previously defined for a compound of the formula (I).

In a typical procedure, the compound of the formula (V) is first deprotonated with approximately one mole equivalent of a suitable base, e.g. lithium hexamethyldisilylazide, and in a suitable aprotic organic solvent, e.g. tetrahydrofuran, and then reacted with a compound of the formula:

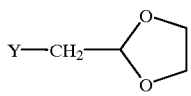  (IX)

wherein Y is a suitable leaving group, e.g. bromo, optionally in the presence of a suitable catalyst, e.g. tetra-n-butylammonium iodide. The alkylated compound produced is then deprotonated with approximately one equivalent of a suitable base, e.g. lithium hexamethyldisilylazide, and in a suitable aprotic organic solvent, e.g. tetrahydrofuran, and then further alkylated with a compound of the formula:

$$Y^1\text{—}CH_2CH_2CO_2R^1 \quad (X)$$

wherein $Y^1$ is a suitable leaving group, e.g. halo, preferably chloro, bromo or iodo, methanesulphonyloxy, trifluoromethanesulphonyloxy or para-toluenesulphonyloxy, and $R^1$ is $C_1$–$C_4$ alkyl, preferably methyl or ethyl. The ester produced can then be hydrolysed to the corresponding carboxylic acid of the formula (VI) under conventional conditions, e.g. using a suitable aqueous mineral acid or base, preferably sodium hydroxide.

The alkylation with the compound of the formula (X) can be carried out in situ, i.e. without isolating the alkylated compound produced by the reaction of the compounds of the formula (V) and (IX). The ester produced also does not need to be isolated and can be hydrolysed to the carboxylic acid of the formula (VI) in the work-up procedure.

If desired, the (R) and (S) enantiomers of the compound of the formula (VI) may be separated by reaction of the carboxylic acid of the formula (VI) with a suitable optically active base, e.g. (R)-(+)- or (S)-(−)-alpha-methylbenzylamine, followed by isolation of the desired optically pure enantiomer(s) using conventional procedures. Preferably, (S)-(−)-alpha-methylbenzylamine is used for the resolution and the salt obtained is not converted to the free acid of the formula (VI) but is used directly in the next cyclisation step.

The compound of the formula (VI) is converted to the piperidin-2-one of the formula (VII) by reductive cyclisation using a suitable catalyst, e.g. platinum oxide, under acidic conditions, e.g. using acetic acid as the solvent, under an atmosphere of hydrogen.

The piperidin-2-one of the formula (VII) can then be N-alkylated with a compound of the formula:

$$R\text{—}X\text{—}Y^2 \quad (XI)$$

wherein R and X are as previously defined for a compound of the formula (I) and $Y^2$ is a suitable leaving group, e.g. halo, preferably chloro, bromo or iodo, methanesulphonyloxy or para-toluenesulphonyloxy, in the presence of a suitable base, e.g. potassium hydroxide, and in a suitable solvent, e.g. dimethyl sulphoxide, to provide a compound of the formula (VIII).

A compound of the formula (VIII) can be directly converted to an aldehyde of the formula (II) by acidic hydrolysis, e.g. using aqueous hydrochloric acid, in the presence of a suitable solvent, e.g. tetrahydrofuran.

Alternatively, a compound of the formula (VIII) can be first converted to a dimethyl acetal of the formula (VIIIA) by treatment with a suitable acidic ion exchange resin, e.g. AMBERLYST 15 (trade mark), in a suitable solvent, e.g. methanol. The acetal can then be converted to an aldehyde of the formula (II) by treatment with a suitable acid, e.g. aqueous hydrochloric acid, in the presence of a suitable solvent, e.g. tetrahydrofuran.

The compounds of the formula (XI) used in this method may be prepared by conventional procedures.

The aldehydes of the formula (II) can also be prepared by the method shown in Scheme 2:

Scheme 2

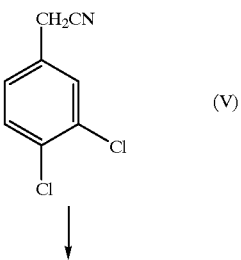  (V)

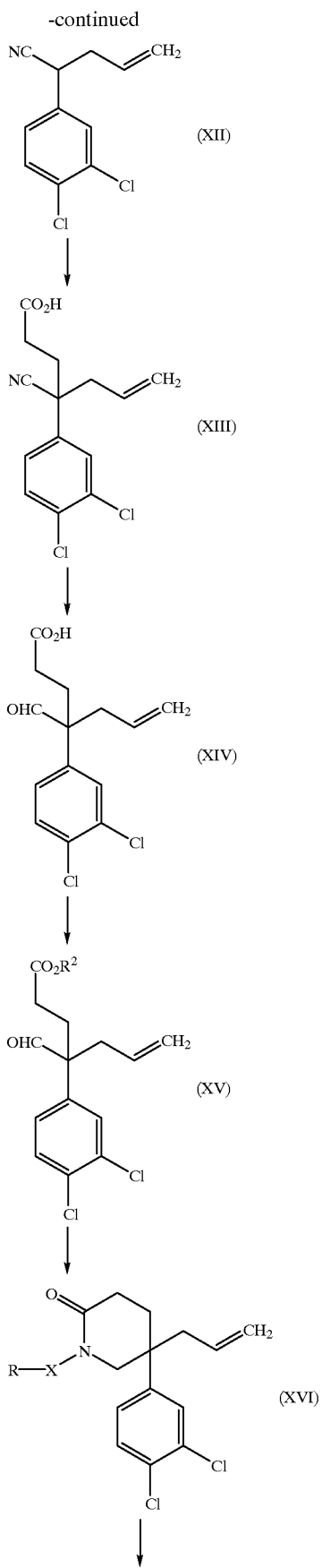

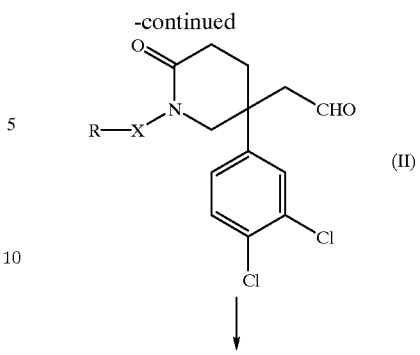

wherein R and X are as previously defined for a compound of the formula (I) and $R^2$ is $C_1$–$C_4$ alkyl, preferably methyl or ethyl.

In a typical procedure, a compound of the formula (V) is first deprotonated with a suitable base and then alkylated with a compound of the formula:

$$CH_2=CHCH_2-Y^3 \hspace{2cm} (XVII)$$

wherein $Y^3$ is a suitable leaving group, e.g. halo, preferably, bromo, methanesulphonyloxy or p-toluenesulphonyloxy. The reaction is preferably carried out by first deprotonating a compound of the formula (V) using an aqueous solution of sodium hydroxide in the presence of a suitable organic solvent, e.g. cyclohexane, followed by alkylation using allyl bromide in the presence of a phase transfer catalyst, preferably tetra-n-butylammonium chloride.

The compound of the formula (XII) prepared is then first deprotonated with a suitable base, e.g. sodium hydride, and then alkylated with a base salt of a compound of the formula:

$$Y^4-CH_2CH_2-CO_2H \hspace{2cm} (XVIII)$$

wherein $Y^4$ is a suitable leaving group, e.g. halo, preferably chloro or bromo, the reaction being carried out in a suitable aprotic organic solvent, e.g. tetrahydrofuran. Treatment with acid in the work-up procedure provides the desired carboxylic acid. Preferably, a sodium salt of a compound of the formula (XVIII) is used.

If desired, the (R) and (S) enantiomers of the compound of the formula (XIII) prepared may be separated by reaction of the compound of the formula (XIII) with a suitable optically active base, e.g. R-(+)- or (S)-(–)-1-(1-naphthyl) ethylamine, followed by isolation of the desired optically active enantiomer(s) using conventional procedures.

The compound of the formula (XIII) can be converted to an aldehyde of the formula (XIV) by reduction using a suitable reducing agent, e.g. diisobutylaluminium hydride, in a suitable organic solvent, e.g. toluene, followed by hydrolysis of the intermediate complex with an aqueous solution of a suitable acid, e.g. citric acid.

Esterification of the compound of the formula (XIV) can be achieved using conventional conditions, e.g. by first forming an activated ester derivative using 1-hydroxybenzotriazole and 1-(3-dimethylaminopropyl)-3-ethylcarbodiimide using dichloromethane as solvent, followed by the addition of a $C_1$–$C_4$ alkanol (i.e. a compound of the formula $R^2OH$).

Reductive amination of a compound of the formula (XV) using a compound of the formula:

$$R-X-NH_2, \hspace{2cm} (XIX)$$

wherein R and X are as previously defined for a compound of the formula (I), in the presence of a suitable reducing agent, e.g. sodium triacetoxyborohydride, and a suitable acid, e.g. acetic acid, and in a suitable solvent, e.g. tetrahydrofuran, provides an intermediate secondary amine that can be cyclised in situ to give a piperidone of the formula (XVI).

A piperidone of the formula (XVI) can be converted to an aldehyde of the formula (II) using a conventional ozonolysis technique.

The compounds of the formula (XIX) used in this method can be prepared by conventional procedures.

An alternative method for converting a compound of the formula (XV) to a compound of the formula (XVI) is shown in Scheme 3:

Scheme 3

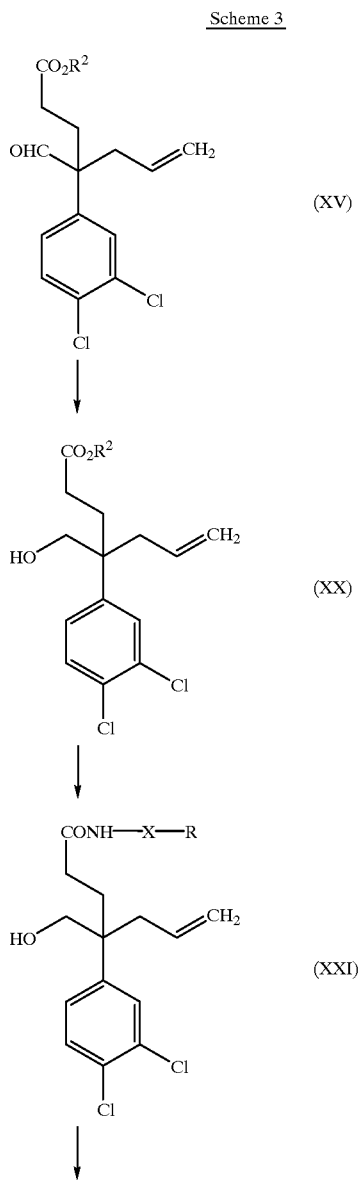

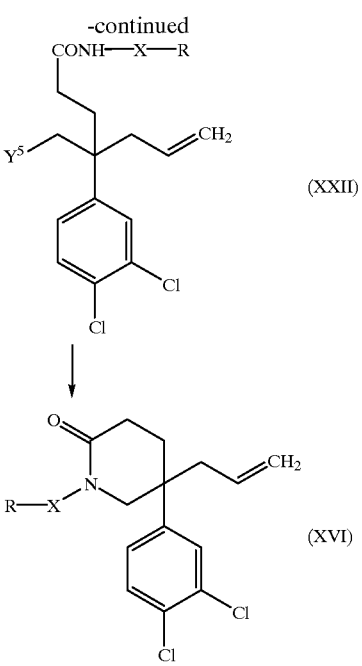

wherein R and X are as previously defined for a compound of the formula (I), $R^2$ is $C_1$–$C_4$ alkyl, preferably methyl or ethyl, and $Y^5$ is a suitable leaving group, e.g. methanesulphonyloxy or para-toluenesulphonyloxy.

In a typical procedure, an aldehyde of the formula (XV) is reduced to a alcohol of the formula (XX) using a suitable reducing agent, e.g. sodium triacetoxyborohydride, in a suitable solvent, e.g. tetrahydrofuran, and in the presence of a suitable acid, e.g. acetic acid.

An ester of the formula (XX) can be converted to an amide of the formula (XXI) under conventional conditions such as by reaction with a compound of the formula (XIX) at an elevated temperature, optionally in the presence of a suitable solvent, e.g. toluene or dimethylformamide.

Conventional functional group interconversion of a compound of the formula (XXI) can provide a compound of the formula (XXII). For example, to obtain a compound of the formula (XXII) where $Y^5$ is methanesulphonyloxy, a compound of the formula (XXI) is reacted with methanesulphonyl chloride in the presence of a suitable acid acceptor, e.g. triethylamine, and in a suitable solvent, e.g. dichloromethane.

A compound of the formula (XXII) is then first N-deprotonated using a suitable base, e.g. sodium hydride, and then cyclised in situ to provide a piperidone of the formula (XVI), the reaction being carried out in a suitable solvent, e.g. tetrahydrofuran.

Further methods for the preparation of the aldehydes of the formula (II) are described in International Patent Application Publication no. WO96/05193, the teaching of which is incorporated herein by reference in this respect.

2) The compounds of the formula (I) can be prepared by alkylation of a N-deprotonated form of a compound of the formula:

(XXIII)

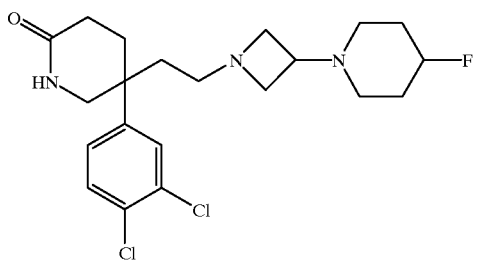

with a compound of the formula:

R—X—Y² (XI)

wherein R, X and Y² are as previously defined for a compound of the formula (XI).

In a typical procedure, a compound of the formula (XXIII) is first deprotonated with a suitable base, e.g. sodium hydride, and then alkylated in situ with a compound of the formula (XI) where Y² is preferably bromo or methanesulphonyloxy. The reaction is typically carried out in a suitable solvent, e.g. dimethylformamide.

Alternatively, the reaction can be carried out by reacting the starting materials of the formulae (XXIII) and (XI) together in the presence of a suitable base, e.g. potassium hydroxide, and in a suitable solvent, e.g. dimethylsulphoxide, at about room temperature. If a compound of the formula (XI) where Y² is chloro is used, potassium iodide may also be added to increase the rate of reaction.

The starting materials of the formula (XXIII) can be prepared by conventional methods such as by adaptation of the preparation described in Method (1), Scheme 1, to convert a compound of the formula (VII) directly to the corresponding aldehyde, followed by reductive amination thereof with a compound of the formula (III), or an acid addition salt thereof, by the procedure of Method (1).

The starting compounds of the formula (XI) can be prepared by conventional methods.

3) The compounds of the formula (I) can be prepared by reaction of a compound of the formula:

(XXIV)

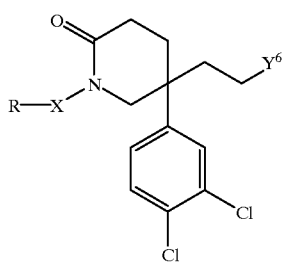

wherein R and X are as previously defined for a compound of the formula (I) and Y⁶ is a suitable leaving group, e.g. chloro, bromo, iodo, methanesulphonyloxy, trifluoromethanesulphonyloxy or p-toluenesulphonyloxy, with a compound of the formula (III). The compound of the formula (III) may be generated in situ from an acid addition salt thereof using a suitable acid acceptor.

In a typical procedure, a compound of the formula (XXIV) is reacted with a compound of the formula (III), or an acid addition salt thereof, in the presence of a suitable acid acceptor, e.g. triethylamine or potassium carbonate, in a suitable solvent, e.g. acetonitrile.

The starting materials of the formula (XXIV) can be prepared by first reducing the aldehydes of the formula (II) to the corresponding primary alcohols, then converting the hydroxy group thereof to the required leaving group Y⁶ using conventional conditions.

4) The compounds of the formula (I) can be prepared by intramolecular dehydration of a compound of the formula:

(XXV)

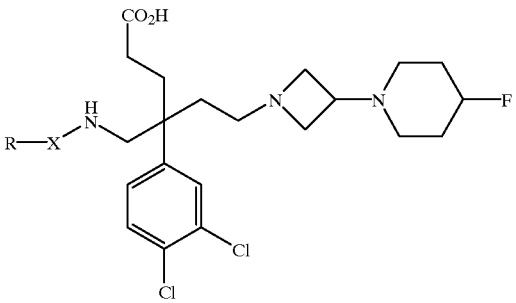

wherein R and X are as previously defined for a compound of the formula (I).

In a typical procedure, the dehydration is carried out under Dean-Stark conditions in a suitable solvent, e.g. toluene, and in the presence of a suitable acid, e.g. p-toluenesulphonic acid. Alternatively, the dehydration can be carried out by stirring a solution of a compound of the formula (XXV) in a suitable solvent, e.g. dichloromethane, in the presence of a dehydrating agent such as silica gel.

The starting materials of the formula (XXV) can be prepared by conventional methods.

5) The compounds of the formula (I) can be prepared by intramolecular cyclisation of a compound of the formula:

(XXVI)

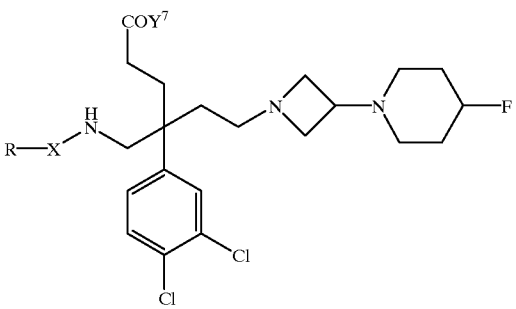

wherein R and X are as previously defined for a compound of the formula (I) and Y⁷ is a suitable leaving group, e.g. $C_1$–$C_4$ alkoxy, benzyloxy, imidazol-1-yl or benzotriazol-1-yloxy.

In typical procedures:
(i) where Y⁷ is $C_1$–$C_4$ alkoxy or benzyloxy, a solution of a compound of the formula (XXVI) in a suitable solvent, e.g. methanol or ethanol, is heated at about the reflux temperature of the solvent;
(ii) where Y⁷ is imidazol-1-yl, a compound of the formula (XXVI) is obtained by reacting a compound of the formula (XXV) with 1,1'-carbonyldiimidazole in a suitable solvent, e.g. dichloromethane, and in situ cyclisation of the intermediate imidazolide provides the required product; and
(iii) where Y⁷ is benzotriazol-1-yloxy, a compound of the formula (XXVI) is derived in situ by reacting a compound of the formula (XXV) with 1-hydroxybenzotriazole in the presence of a suitable dehydrating agent, e.g. 1,3-dicyclohexylcarbodiimide, and in a suitable solvent, e.g. dichloromethane, and in situ cyclisation of the intermediate activated ester provides the required product.

The starting materials of the formula (XXVI) can be prepared by conventional methods such as from a compound of the formula (XXV), examples of which are described above.

6) The compounds of the formula (I) can be prepared by reductive amination using as starting materials a compound of the formula:

(XXVII)

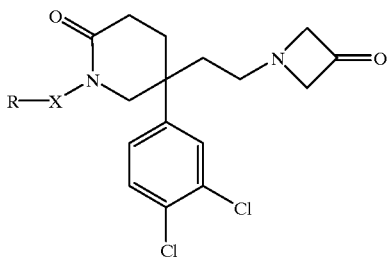

wherein R and X are as previously defined for a compound of the formula (I), and a compound of the formula:

(XXVIII)

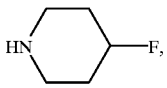

or an acid addition salt thereof. The reaction is preferably carried out in the presence of a suitable acid, e.g. acetic acid. The reaction is typically carried out using a similar procedure to that described in Method (1). The reaction proceeds via an intermediate iminium salt of the formula:

(XXIX)

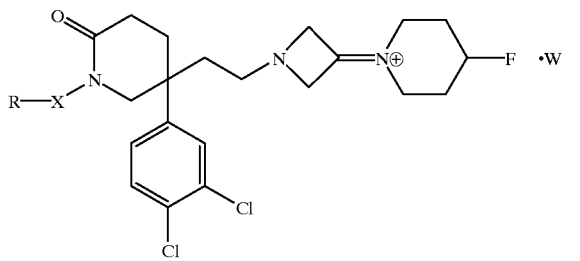

wherein W is an anion (e.g. acetate) derived from a suitable acid (e.g. acetic acid) and R and X are as previously defined for a compound of the formula (I), which may be stable and isolatable.

The reaction is preferably carried out without isolation of a compound of the formula (XXIX) in which case it is reduced in situ to provide a compound of the formula (I).

The starting materials of the formula (XXVII) may be prepared by oxidation of the corresponding azetidin-3-ol derivatives (which can be prepared by reaction of a compound of the formula (XXIV) with azetidin-3-ol using a conventional procedure) using standard conditions, e.g. using pyridinium chlorochromate or tetrapropylammonium perruthenate as the oxidising agent.

7) The compounds of the formula (I) can be prepared by reductive cyclisation of a compound of the formula:

(XXX)

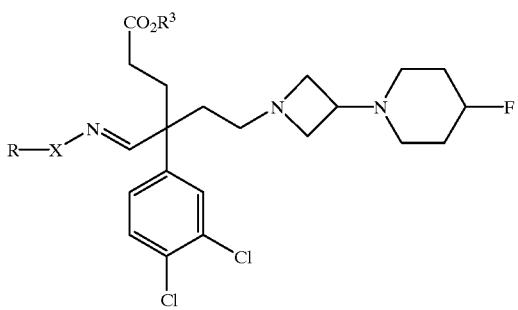

wherein R and X are as previously defined for a compound of the formula (I) and $R^3$ is a suitable ester-forming group, e.g. $C_1$–$C_4$ alkyl, preferably methyl or ethyl, or benzyl.

In a typical procedure, a compound of the formula (XXX) is first generated in situ by reacting a compound of the formula:

(XXXI)

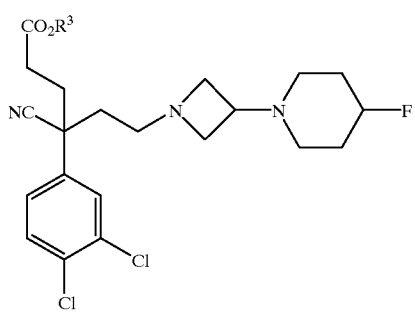

wherein $R^3$ is as previously defined for a compound of the formula (XXX) with a compound of the formula (XIX) wherein R and X are as previously defined for a compound of the formula (I), and then the reductive cyclisation is facilitated by the presence of a suitable reducing agent, e.g. Raney nickel. The reaction is carried out in a suitable solvent, e.g. methanol or ethanol, and under an atmosphere of hydrogen.

The starting materials of the formula (XXXI) can be prepared by conventional methods.

8) The compounds of the formula (I) can be prepared by catalysed carbonyl addition-cyclisation of a compound of the formula:

(XXXII)

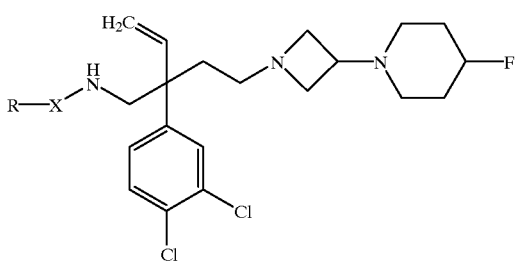

wherein R and X are as previously defined for a compound of the formula (I).

The reaction is typically carried out under an atmosphere of carbon monoxide using a suitable catalyst, e.g. tetrakistriphenylphosphinepalladium (O), a suitable base, e.g. triethylamine, and in a suitable organic solvent, e.g. tetrahydrofuran, at about room temperature.

The compounds of the formula (XXXII) may be prepared by conventional methods.

9) The compounds of the formula (I) can be prepared by reductive cyclisation of a compound of the formula:

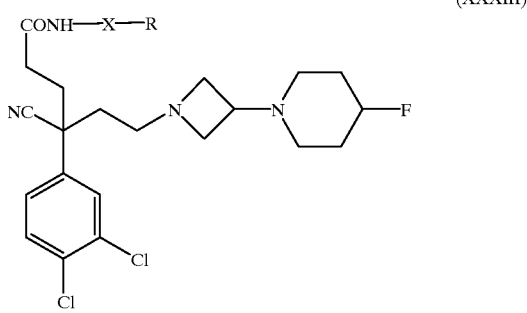

(XXXIII)

wherein X and R are as previously defined for a compound of the formula (I).

In a typical procedure, the reductive cyclisation is carried out using a suitable catalyst, e.g. platinum oxide, under a hydrogen atmosphere and in a suitable solvent, e.g. acetic acid, at room temperature and 414 kPa (60 p.s.i.).

The compounds of the formula (XXXIII) may be generated by conventional procedures such as from a compound of the formula (XXXI).

All of the above reactions and the preparations of novel starting materials used in the preceding methods are conventional and appropriate reagents and reaction conditions for their performance or preparation as well as procedures for isolating the desired products will be well known to those skilled in the art with reference to literature precedents and the Examples and Preparations hereto.

A pharmaceutically acceptable acid addition salt of a compound of the formula (I) may be readily prepared by mixing together solutions of a compound of the formula (I) and the desired acid. The salt may precipitate from solution and be collected by filtration or may be recovered by evaporation of the solvent.

The affinity of the compounds of formula (I) and their salts for the human $NK_1$ receptor can be tested in vitro by testing their ability to inhibit [$^3$H]-Substance P binding to membranes prepared from the human IM9 cell line expressing the human $NK_1$ receptor using a modification of the method described in McLean, S. et al, J. Pharm. Exp. Ther., 267, 472–9 (1993) in which whole cells were used.

The affinity of the compounds of the formula (I) and their salts for the human $NK_2$ receptor can be tested in vitro by testing their ability to compete with [$^3$H] or [$^{125}$I]NKA (neurokinin A) for binding to membranes prepared from Chinese hamster ovary cells expressing the cloned human $NK_2$ receptor. In this method, washed Chinese hamster ovary cell membranes are prepared as described for the previous method where IM9 cells are used instead. The membranes are incubated (90 min, 25° C.) with [$^3$H] or [$^{125}$I]NKA and with a range of concentrations of the test compound. Non-specific binding was determined in the presence of 10 μM NKA.

The $NK_2$ receptor antagonist activity of the compounds of the formula (I) can be tested, in vitro, by testing their ability to antagonise the contractile effects of the selective $NK_2$ receptor agonist [βAla$^8$]NKA$_{(4-10)}$ in the rabbit pulmonary artery, using the method of Patacchini and Maggi, Eur. J. Pharmacol., 236, 31–37 (1993).

The compounds of the formula (I) and their salts can be tested for $NK_2$ receptor antagonist activity, in vivo, by testing their ability to inhibit bronchoconstriction induced by [βAla$^8$]NKA$_{(4-10)}$ in the anaesthetised guinea pig, using the method described by Murai et al, J. Pharm. Exp. Ther., 262, 403–408 (1992) or Metcalfe et al, Br. J. Pharmacol., 112, 563P (1994).

The compounds of the formula (I) and their salts can be tested for $NK_3$ receptor antagonist activity, in vitro, by testing their ability to antagonise the contractile effects of the selective $NK_3$ receptor agonist senktide in the guinea pig ileum using the method of Maggi et al, Br. J. Pharmacol., 101, 996–1000 (1990). For human use, the compounds of the formula (I) and their salts can be administered alone, but will generally be administered in admixture with a pharmaceutically acceptable diluent or carrier selected with regard to the intended route of administration and standard pharmaceutical practice. For example, they can be administered orally, including sublingually and buccally, in the form of tablets containing such excipients as starch or lactose, or in capsules or ovules either alone or in admixture with excipients, or in the form of elixirs, solutions or suspensions containing flavouring or colouring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral and parenteral administration to human patients, the daily dosage level of the compounds of the formula (I) and their salts will be from 0.001 to 20, preferably from 0.01 to 20, and most preferably from 0.1 to 10, mg/kg (in single or divided doses). Thus tablets or capsules of the compounds will contain from 0.1 to 500, preferably from 10 to 200, mg of active compound for administration singly or two or more at a time, as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited, and such are within the scope of this invention.

Alternatively, the compounds of the formula (I) can be administered intranasally, by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin, or they can be incorporated, at a concentration of between 1 and 10%, into an ointment consisting of a white wax or white soft paraffin base together with such stabilizers and preservatives as may be required. The compounds of the formula (I) may also be administered in the form of an aerosol spray presentation or by using a dry powder inhaler formulation.

It is to be appreciated that reference to treatment includes prophylaxis as well as the alleviation of established symptoms of the disease.

Thus the invention further provides:-

(i) a pharmaceutical composition comprising a compound of the formula (I), or a pharmaceutically acceptable acid addition salt thereof, together with a pharmaceutically acceptable diluent or carrier;

(ii) a compound of the formula (I), or a pharmaceutically acceptable acid addition salt or composition thereof, for use as a medicament;

(iii) the use of a compound of the formula (I), or of a pharmaceutically acceptable acid addition salt or composition thereof, for the manufacture of a medicament for the treatment of a disease by producing an antagonist effect on a tachykinin acting at the human $NK_1$, $NK_2$ or $NK_3$ receptor, or any combination thereof;

(iv) use as in (iii) where the disease is an inflammatory disease such as arthritis, psoriasis, asthma or inflammatory bowel disease, a central nervous system (CNS) disorder such as anxiety, depression, dementia or psychosis, a gastro-intestinal (GI) disorder such as functional bowel disease, irritable bowel syndrome, gastro-oesophageal reflux, faecal incontinence, colitis or Crohn's disease, an urogenital tract disorder such as incontinence, hyperreflexia or cystitis, a pulmonary disorder such as chronic obstructive airways disease, an allergy such as eczema, contact dermatitis or rhinitis, a hypersensitivity disorder such as to poison ivy, a peripheral neuropathy such as diabetic neuropathy, neuralgia, causalgia, painful neuropathy, a burn, herpetic neuralgia or post-herpetic neuralgia, cough or acute or chronic pain;

(v) a method of treatment of a human to treat a disease by producing an antagonist effect on a tachykinin acting at the human $NK_1$, $NK_2$ or $NK_3$ receptor, or any combination thereof, which comprises treating said human with an effective amount of a compound of the formula (I) or with a pharmaceutically acceptable acid addition salt or composition thereof;

(vi) a method as in (v) where the disease is an inflammatory disease such as arthritis, psoriasis, asthma or inflammatory bowel disease, a central nervous system (CNS) disorder such as anxiety, depression, dementia or psychosis, a gastro-intestinal (GI) disorder such as functional bowel disease, irritable bowel syndrome, gastro-oesophageal reflux, faecal incontinence, colitis or Crohn's disease, an urogenital tract disorder such as incontinence, hyperreflexia or cystitis, a pulmonary disorder such as chronic obstructive airways disease, an allergy such as eczema, contact dermatitis or rhinitis, a hypersensitivity disorder such as to poison ivy, a peripheral neuropathy such as diabetic neuropathy, neuralgia, causalgia, painful neuropathy, a burn, herpetic neuralgia or post-herpetic neuralgia, cough or acute or chronic pain; and (vii) a compound of the formula (IV), (VIIIA), (XXIII), (XXV), (XXVI), (XXVII), (XXIX), (XXX), (XXXI), (XXXII) or (XXXIII) or a para-toluenesulphonate salt of a compound of the formula (III).

The following Examples illustrate the preparation of the compounds of the formula (I):

EXAMPLE 1

5(S)-5-(3,4-Dichlorophenyl)-1-(4,4-difluorocyclohexylmethyl)-5-(2-[3-(4-fluoropiperidin-1-yl]azetidin-1-yl)ethylpiperidin-2-one

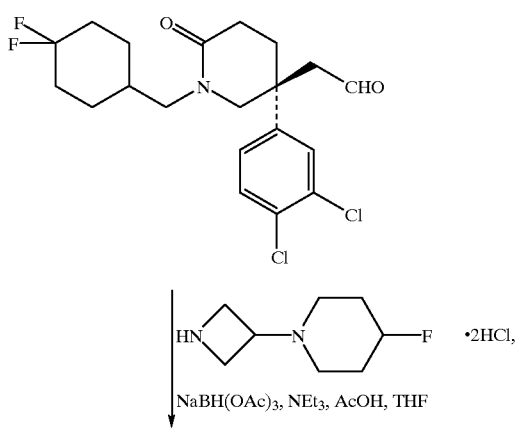

-continued

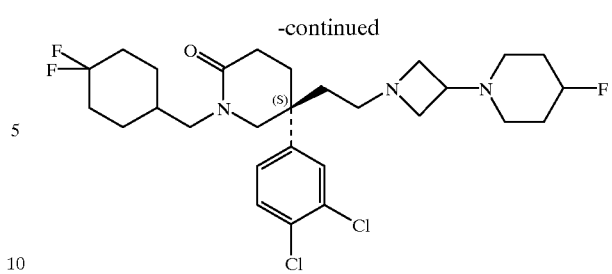

To a solution of the aldehyde (see Preparations 1 and 15) (125 mg, 0.299 mmol) and 3-(4-fluoropiperidin-1-yl) azetidine dihydrochloride (see Preparation 3) (70 mg, 1.01 mol equiv.) in tetrahydrofuran (8 ml) under nitrogen was added triethylamine (0.092 ml, 2.2 mol equiv.). After stirring for one hour, sodium triacetoxyborohydride (0.095 g, 1.5 mol equiv.) was added followed by glacial acetic acid (0.017 ml, 1 mol equiv.) and the mixture was stirred for 18 hours. The solvent was removed by evaporation under reduced pressure and the residue was partitioned between saturated aqueous sodium bicarbonate solution (20 ml) and ethyl acetate (20 ml). The aqueous portion was separated and further extracted with ethyl acetate (2×20 ml). The organic layers were then combined and dried over sodium sulphate. The mixture was filtered and the solvent removed from the filtrate by evaporation under reduced pressure. The residue was purified by flash column chromatography on silica gel eluting with methanol:dichloromethane (2:25, by volume) to provide the title compound (103 mg). TLC Rf=0.18 (silica, methanol:dichloromethane, 1:19, by volume). LRMS 561.7 $(m+1)^+$.

Found: C,59.49; H, 6.81; N, 7.38. $C_{28}H_{38}N_3OF_3Cl_2$·0.625 $CH_2Cl_2$ requires C,59.56; H, 6.79; N, 7.43%.

$^1$H-NMR (CDCl$_3$): δ=1.2–1.45 (m,2H), 1.5–2.25 (m,19H), 2.3–2.5 (m,3H), 2.6–2.8 (m,2H), 2.85–3.0 (m,1H), 3.15–3.25 (m,1H), 3.3–3.5 (m,4H), 3.5–3.6 (m,2H), 4.5–4.8 (m,1H), 7.0–7.1 (m,1H), 7.2–7.5 (m,2H) ppm.

$[\alpha]_d^{25}$=−28° (c=0.001 in methanol, cell length=1 decimeter).

EXAMPLES 2 TO 4

The compounds of the following tabulated Examples of the general formula:

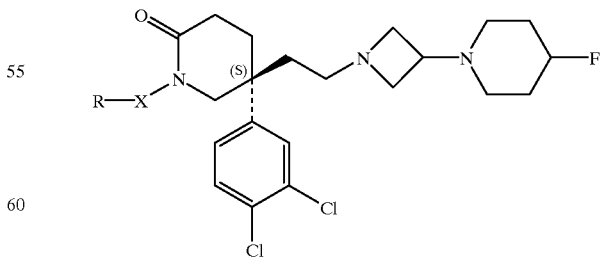

were prepared by a similar method to that of Example 1 using the appropriate aldehyde starting materials (see Preparations 2,7 and 8).

| EXAMPLE NO. | R-X- | LRMS | $^1$H-NMR |
|---|---|---|---|
| 2[1] | (cyclohexylmethyl) | 510 (m)$^+$ | $^1$H-NMR (CDCl$_3$): δ = 1.0–2.3 (m,23 H), 2.3–2.5 (m,3 H), 2.6–2.8 (m,2 H), 2.8–3.0 (m,1H), 3.1–3.2 (m,1 H), 3.3–3.6 (m,3 H), 4.4–4.8 (m,2 H), 7.05–7.15 (m,1 H), 7.3–7.45 (m,2 H) ppm. |
| 3[2] | (cyclopropylspirocyclopentylmethyl) | — | $^1$H-NMR (CDCl$_3$): δ = 0.4–0.6 (m,4 H), 1.4–1.6 (m,1 H), 1.8–2.3 (m,23 H), 2.3–2.5 (m,2 H), 2.6–2.8 (m,1 H), 2.8–3.0 (m,1 H), 3.3–3.5 (m,3 H), 3.6–3.7 (m,1 H), 4.5–4.8 (m,1 H), 7.1–7.2 (m,1 H), 7.35–7.45 (m,2 H) ppm. |
| 4[3] | (cyclopropylethyl) | 496 (m)$^+$ | $^1$H-NMR (CDCl$_3$): δ = 0.05–0.2 (m,2 H), 0.4–0.55 (m,2 H), 0.6–0.8 (m,1 H), 1.2–2.3 (m,15 H), 2.3–2.5 (m,3 H), 2.6–2.8 (m,2 H), 2.8–2.95 (m,1 H), 3.2–3.5 (m,4 H), 3.5–3.7 (m,2 H), 4.55–4.8 (m,1 H), 7.0–7.1 (m,1 H), 7.2–7.45 (m,2 H) ppm. |

Footnotes
1. The chromatography eluant was ethyl acetate:methanol:concentrated aqueous ammonia solution (78.4:20:1.6, by volume).
2. The chromatography eluant was dichloromethane:methanol (19:1 changing to 9:1, by volume).
3. The chromatography eluant was dichloromethane:methanol (25:2, by volume).

EXAMPLE 5

5(S)-5-(3,4-Dichlorophenyl)-1-(4,4-difluorocyclohexylmethyl)-5-(2-[3-(4-fluoropiperidin-1-yl)]azetidin-1-yl)ethylpiperidin-2-one

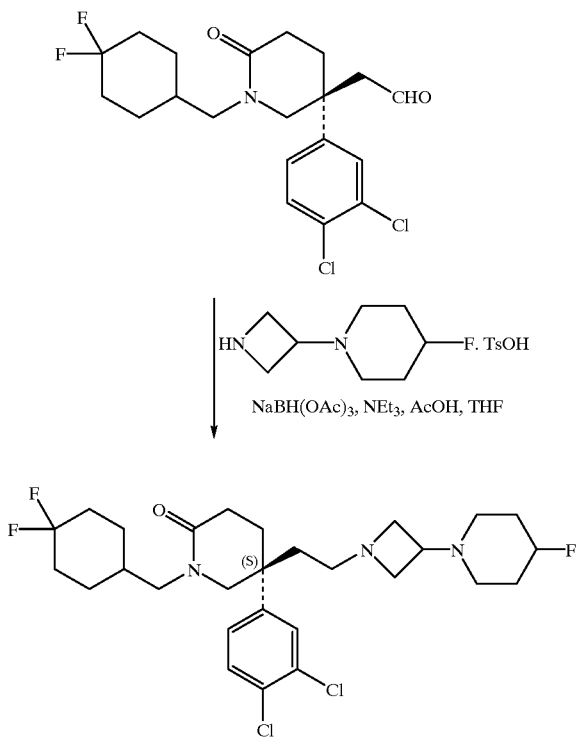

To a slurry of the azetidine (see Preparation 13) (241 g) in tetrahydrofuran (1700 ml) was added triethylamine (118 ml) and the mixture stirred for 1 hour. A solution of the aldehyde (see Preparations 1 and 15) (294.1 g) in THF (800 ml) was then added and the mixture stirred for 3 hours before adding sodium triacetoxyborohydride (194 g) and glacial acetic acid (40.3 ml).

The slurry was stirred for 2 hours, water (1700 ml) added and the mixture combined with the reaction product from an identical experiment starting from 294 g of the aldehyde and 241 g of the azetidine.

The pH of the mixture was adjusted to 9 with saturated aqueous sodium bicarbonate solution and then it was extracted with ethyl acetate (3×2000 ml). The combined organic layers were concentrated under reduced pressure to provide the impure title compound as a yellow foam (808 g). HPLC analysis showed this to contain 92.4% (by weight) of the title compound.

EXAMPLE 6

5(S)-5-(3,4-Dichlorophenyl)-1-(4,4-difluorocyclohexylmethyl)-5-(2-[3-(4-fluoropiperidin-1-yl)]azetidin-1-yl)ethylpiperidin-2-one disuccinate A solution of the compound of Example 5 (752.5 g) in acetone (1500 ml) was filtered and further acetone (1500 ml) added to the filtrate. Succinic acid (279 g) was added and the solution stirred at room temperature for 1 hour, then at 0° C. for 1 hour. The resulting solid was filtered off, washed with acetone and dried to provide the title compound as a white powder (919.5 g).

The following Preparations illustrate the synthesis of certain intermediates used in the preparation of the compounds of the preceding Examples:

Preparation 1

5(S)-5-(3,4-Dichlorophenyl)-1-(4,4-difluorocyclohexylmethyl)-5-formylmethylpiperidin-2-one

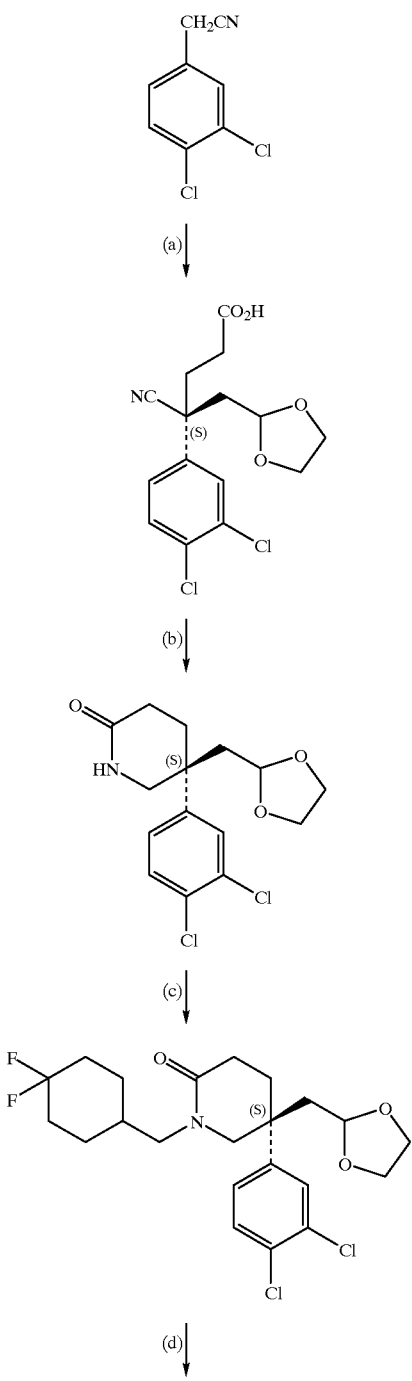

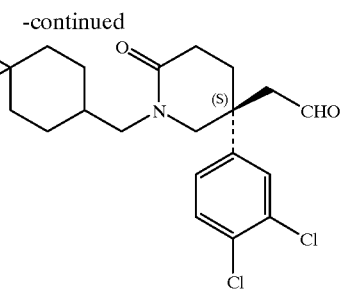

(a) 4(S)-4-Cyano4-(3,4-dichlorophenyl)-5-(1,3-dioxolan-2-yl)pentan-1-oic acid

To a 1.0M solution of lithium hexamethyldisilylazide in tetrahydrofuran (4.69 l) at 5° C. under nitrogen was added a solution of 3,4-dichlorophenylacetonitrile (750 g, 4.28 moles) in tetrahydrofuran (750 ml), dropwise, over 45 minutes. The reaction was allowed to stir for 2 hours. The reaction was cooled again to 5° C. and a solution of 2-bromomethyl-1,3-dioxolane (782 g) in tetrahydrofuran (780 ml) added, dropwise, over fifty minutes. Tetra-n-butylammonium iodide (75 g) was added, portionwise, and the mixture allowed to warm to room temperature and stirred for 14 hours. The reaction was then cooled to 5° C. and 1.0M solution of lithium hexamethyidisilylazide in tetrahydrofuran (4.69l) was added, dropwise. The mixture was stirred for 5 hours at room temperature. The solution was cooled to 5° C. and a solution of ethyl 3-bromopropanoate (840.5 g) in tetrahydrofuran (840 ml) was added, dropwise, over 50 minutes. The reaction was allowed to stir for 14 hours. The reaction mixture was cooled to 5° C. and 1.5M aqueous sodium hydroxide solution (containing 255 g of sodium hydroxide) was added and the mixture stirred for 14 hours. Water (5 l) was added and the mixture was extracted with ethyl acetate (2×3 l). The combined organic extracts were washed with water (2×5 l). The aqueous phases were combined and acidified to pH1 using 5N aqueous hydrochloric acid solution and then extracted with ethyl acetate (2×3 l).

The combined organic extracts were concentrated under reduced pressure to a concentration of approximately 3 ml/g based on the theoretical yield of the product.

The above experimental procedure was then repeated on an identical scale.

To the combined organic solutions from both reactions was added (S)-(−)-alpha-methylbenzylamine (1.13 kg) and the mixture stirred for 14 hours. The thick slurry was then stirred with cooling in an ice-bath for 2 hours, filtered, the solid washed with ethyl acetate (2×1 l) and then dried under reduced pressure at 35° C. to give 1.85 kg of material.

A portion of this material (1.34 kg) was dissolved in a mixture of butanone (2 l) and water (503 ml) that was heated under reflux. A further portion of butanone (4.7 l) was added and the solution was allowed to cool slowly to room temperature overnight. The resulting solid was filtered off, washed with butanone (2×1 l) and dried under reduced pressure at 35° C. for 10 hours to give 563 g of material (93.8% e.e.). A further recrystallisation from butanone/water gave the title compound as a (S)-(−)-alpha-methylbenzylamine salt in 99.8% e.e. To a stirred solution of this salt in ethyl acetate and water was added 5N aqueous hydrochloric acid solution until pH1 was achieved. The mixture was stirred for a further 30 minutes, the layers separated and the aqueous phase extracted with ethyl acetate.

The combined organic layers were washed with water and the solvent removed by evaporation under reduced pressure to give the title compound.

$^1$H-NMR (CDCl$_3$): δ=2.05–2.35 (m,4H), 2.4–2.65 (m,2H), 3.7–4.0 (m,4H), 4.75–4.85(m,1H), 7.25–7.55 (m,3H), 9.9 (s.br., 1H, acid) ppm.

(b) 5(S)-5-(3,4-Dichlorophenyl)-5-(1,3-dioxolan-2-ylmethyl)piperidin-2(1H)-one

To a solution of the compound of Preparation 1(a) (13.5 g, 39.22 mmol) in glacial acetic acid (130 ml) was added platinum oxide (1.21 g) and the mixture stirred under an atmosphere of hydrogen at 414 kPa (60 psi) and at room temperature for 17 hours. The catalyst was removed by filtration and a further portion of platinum oxide (1.21 g) added. The reaction mixture was then stirred under an atmosphere of hydrogen at 414 kPa (60 psi) and at room temperature for 48 hours. The catalyst was removed by filtration and the solution concentrated under reduced pressure. The residue was dissolved in ethyl acetate (80 ml) and washed with saturated aqueous sodium bicarbonate solution (2×75 ml). The organic phase was then separated and the solvent removed under reduced pressure. The resulting solid was stirred in a solution of hexane (20 ml) and ethyl acetate (20 ml) for 2 hours at 0° C. and then filtered off to give the title compound (8.15 g).

$^1$H-NMR (CDCl$_3$): δ=1.85–1.95 (m,1H), 2.0–2.25 (m,4H), 2.35–2.4 (m,1H), 3.45–3.55 (m,1H), 3.65–3.75 (m,2H), 3.8–3.9 (m,3H), 4.35–4.4 (m,1H), 6.15 (s.br.,1H), 7.2–7.45 (m,3H) ppm.

(c) 5(S)-5-(3,4-Dichlorophenyl)-1-(4,4-difluorocyclohexylmethyl)-5-(1,3-dioxolan-2-ylmethyl)piperidin-2-one To a stirred mixture of dimethyl sulphoxide (10 ml) and potassium hydroxide (340 mg, 4 mol. equiv.) at room temperature under nitrogen was added a solution of the compound of Preparation 1(b) (500 mg, 1.51 mmol) in dimethyl sulphoxide (5 ml). A solution of the compound of Preparation 9 (381 mg, 1.1 mol. equiv.) in dimethyl sulphoxide (5 ml) was then added and the mixture stirred at room temperature for 16 hours.

This mixture was then combined with that prepared by a similar method to that described above using the compound of Preparation 1(b) (960 mg, 2.9 mmol) and appropriate amounts of the other reagents.

Ethyl acetate (150 ml) was added and the mixture washed with water (3×30 ml) followed by brine (1×30 ml). The organic layer was dried over anhydrous magnesium sulphate, filtered and evaporated to dryness under reduced pressure. The residue was chromatographed using silica gel eluting with n-pentane: ethyl acetate (1:1 changing to 0:1, by volume) to provide the title compound as a white foam (1.07 g). LRMS m/z=462 (m$^+$).

$^1$H-NMR (CDCl$_3$): δ=1.3–1.45 (m,2H), 1.6–1.95 (m,6H), 2.1–2.2 (m,6H), 2.4–2.55 (m,1H), 3.2–3.3 (m,1H), 3.4–3.5 (m,2H), 3.65–3.75 (m,3H), 3.85–3.95 (m,2H), 4.3–4.35 (m,1H), 7.1–7.4 (m,3H) ppm.

(d) 5(S)-5-(3,4-Dichlorophenyl)-1-(4,4-difluorocyclohexylmethyl)-5-formylmethylpiperidin-2-one A solution of the compound of Preparation 1(c) (3.3 g, 7.14 mmol) in tetrahydrofuran (36 ml) and 5N aqueous hydrochloric acid solution (36 ml) was stirred at room temperature under nitrogen for 90 minutes and then heated at 45° C. for a further 90 minutes. The reaction mixture was poured into a mixture of ethyl acetate (40 ml) and saturated aqueous sodium bicarbonate solution (40 ml). The organic phase was separated and the aqueous phase extracted with ethyl acetate (2×30 ml). The organic phases were then combined, dried using sodium sulphate, filtered and the solvent removed from the filtrate by evaporation under reduced pressure to give the title compound (2.97 g) which was used without further purification.

TLC Rf=0.3 (silica, ethyl acetate). LRMS 418 (m)$^+$.

See Preparation 15 for an alternative preparation of this compound.

Preparation 2

5(S)-1-(2-Cyclopropylethyl)-5-(3,4-dichlorophenyl)-5-formylmethylpiperidin-2-one (a) 5(S)-1-(2-Cyclopropylethyl)-5-(3,4-dichlorophenyl)-5-(1,3-dioxolan-2-ylmethyl)piperidin-2-one The title compound was prepared by a similar method to that of Preparation 1(c) using the compound of Preparation 1(b) and the compound of Preparation 10 as the starting materials. LRMS m/z=398 (m+1)$^+$.

$^1$H-NMR (CDCl$_3$): δ=0.1–0.15 (m,2H), 0.45–0.5 (m,2H), 0.6–0.75 (m,1H), 1.5–1.6 (m,2H), 1.9–1.95 (m,1H), 2.1–2.2 (m,4H), 2.35–2.5 (m,1H), 3.3–3.4 (m,1H), 3.5–3.6 (m,1H), 3.65–3.75 (m,4H), 3.85–3.9 (m,2H), 4.35–4.4 (m,1H), 7.1–7.45 (m,3H) ppm.

(b) 5(S)-1-(2-Cyclopropylethyl)-5-(3,4-dichlorophenyl)-5-formylmethylpiperidin-2-one The title compound was prepared by a similar method to that of Preparation 1(d) using the compound of Preparation 2(a) as the starting material. The product obtained was shown to be contaminated with approximately 35 mol % of the dioxolane starting material by $^1$H-NMR spectroscopy.

LRMS m/z=354 (m+1)$^+$.

Preparation 3

3-(4-Fluoropiperidin-1-yl)azetidine dihydrochloride (a) 1-Diphenylmethylazetidin-3-ol A solution of benzhydrylamine (200 ml, 1.16 mol) and epichlorohydrin (186 ml, 1 mol. equiv.) in methanol (600 ml) was stirred at room temperature for five days and then heated at 40° C. for two days. The solvent was removed under reduced pressure, the residue dissolved in isopropyl alcohol (500 ml) and the solution heated under reflux for six hours. The solution was cooled to room temperature and the precipitate filtered off. This solid was partitioned between dichloromethane (400 ml) and saturated aqueous sodium bicarbonate solution (500 ml). The aqueous phase was extracted with dichloromethane (2×400 ml) and the combined organic phases dried over magnesium sulphate. The solution was then filtered and the solvent removed from the filtrate by evaporation under reduced pressure to give the title compound (86 g) as a crystalline solid.

$^1$H-NMR (CDCl$_3$): δ=1.8–2.3 (s,br,1H), 2.85–2.9 (m,2H), 3.5–3.55 (m,2H), 4.35 (s,1H), 4.4–4.5 (m,1H), 7.15–7.4 (m,10H) ppm.

(b) 1-Diphenylmethyl-3-methanesulphonyloxyazetidine

To a solution of 1-diphenylmethylazetidin-3-ol (see Preparation 3(a)) (65.9 g, 275.7 mmol) in dry dichloromethane (700 ml) at 0° C. under nitrogen was added triethylamine (57 ml, 1.5 mol. equiv.). After five minutes, methanesulphonyl chloride (25.6 ml, 1.2 mol. equiv.) was added and the mixture stirred for one hour. Water (300 ml) was then added and the mixture extracted with dichloromethane (3×300 ml). The combined organic layers were dried over magnesium sulphate. The solution was then filtered and the solvent removed from the filtrate by evaporation under reduced pressure. The residue was chromatographed using silica gel eluting with methanol:dichloromethane (1:49, by volume) to give the title compound (73.4 g) as a solid.

$^1$H-NMR (CDCl$_3$): δ=2.95 (s,3H), 3.15–3.25 (m,2H), 3.6–3.65 (m,2H), 4.4 (s,1H), 5.05–5.15 (m,1H), 7.15–7.4 (m,10H) ppm.

(c) 1-Diphenylmethyl-3-(4-hydroxypiperidin-1-yl)azetidine

A solution of 1-diphenylmethyl-3-methanesulphonyoxyazetidine (see Preparation 3(b)) (317 g, 1 mol), diethylisopropylamine (155.1 g, 1.2 mol. equiv.) and 4-hydroxypiperidine (121.2 g, 1.2 mol. equiv.) in acetonitrile (500 ml) was heated under reflux for five hours. The solution was cooled to room temperature and the mixture concentrated under reduced pressure. The residue was partitioned between dichloromethane (1.5 l) and saturated sodium bicarbonate solution (500 ml) and the organic phase separated and washed again with saturated sodium bicarbonate solution (2×500 ml). The organic phase was then washed with 1M aqueous citric acid solution (2×500 ml). The acidic aqueous layer was basified to pH 8.5 using 2N aqueous sodium hydroxide solution (600 ml) at 0° C. and then extracted using dichloromethane (1 l). The combined organic layers were dried over magnesium sulphate, filtered and evaporated under reduced pressure to give the title compound as a gum (309 g). TLC Rf=0.2 (silica, methanol:dichloromethane, 1:19, by volume). LRMS m/z= 323 (m+1)$^+$.

$^1$H-NMR (CDCl$_3$): δ=1.4–1.6 (m,4H), 1.8–2.0 (m,4H), 2.5–2.65 (m,2H), 2.8–3.0 (m,2H), 3.3–3.4 (m,2H), 3.6–3.8 (m,1H), 4.4 (s,1H), 7.1–7.4 (m,10H), ppm.

The above product can be further purified by conversion to a tosylate salt using para-toluenesulphonic acid and acetone as the solvent, the salt being re-converted to the free base before its use in the next step.

(d) 1-Diphenylmethyl-3-(4-fluoropiperidin-1-yl)azetidine

To a solution of diethylaminosulphur trifluoride (170 g, 1.06 mol) at −60° C. in dichloromethane (927 ml) under nitrogen was added a solution of the compound of Preparation 3(c) in dichloromethane (927 ml). The mixture was allowed to warm to room temperature over 2 hours and stirred at room temperature for a further 9 hours. The reaction was then carefully added, dropwise, to aqueous saturated sodium bicarbonate solution (3 l) (an exotherm resulted). The aqueous layer was separated and the organic layer washed with water (2×500 ml). The solvent was removed from the organic layer by evaporation under reduced pressure and the resulting oil purified by chromatography on silica gel eluting with a solvent gradient of dichloromethane changing to dichloromethane:methanol (19.1, by volume) to yield the title compound (172 g). TLC Rf=0.7 (silica, methanol:dichloromethane, 1.19, by volume).

$^1$H-NMR (CDCl$_3$): δ=1.75–2.0 (m,4H), 2.1–2.3 (m,2H), 2.3–2.5 (m,2H), 2.8–3.05 (m,3H), 3.3–3.4 (m,2H), 4.4 (s,1H), 4.5–4.8 (m,1H), 7.1–7.45 (m,10H) ppm.

The above method can be modified by omitting the chromatography step and instead converting the reaction product to a tosylate salt by treatment with para-toluenesulphonic acid using ethyl acetate as the solvent. The tosylate salt obtained may be used directly in the next step.

(e) 3-(4-Fluoropiperidin-1-yl)azetidine dihydrochloride

To a solution of the compound of Preparation 3(d) (170 g) in dry dichloromethane (1 l) at 0° C. under nitrogen was added α-chloroethyl chloroformate (149.6 g, 2 mol. equiv.) and the reaction stirred for 1.5 hours. Methanol (10 ml) was then added and the mixture heated under reflux for 15 minutes. The solvent was then removed by evaporation under reduced pressure and the resultant gum triturated with acetone (3×300 ml). Hot isopropyl alcohol (500 ml) was then added and the mixture heated at 80° C. for 15 minutes. A portion of isopropyl alcohol (150 ml) was then removed by evaporation under reduced pressure and the mixture stirred at 10° C. for 0.5 hour. The resultant solid was filtered off and washed with cold isopropyl alcohol (30 ml). This solid was triturated with acetone (600 ml), filtered and dried at 70° C. for 4 hours to provide the title compound (69.4 g).

$^1$H-NMR (d$_6$-DMSO): δ=1.9–2.3 (m,4H), 2.8–4.6 (m,9H), 4.7–5.2 (m,1H), 9.1 (s,br.,1H), 9.8 (s.br.,1H), 12.6 (s,br.1H) ppm.

See Preparation 13 for the preparation of the corresponding tosylate salt by transfer hydrogenation using the tosylate obtained by the modified method of Preparation 3(d) as the starting material.

Preparation 4

Methyl 4(S)-4-(3,4-dichlorophenyl)-4-formylhept-6-enoate

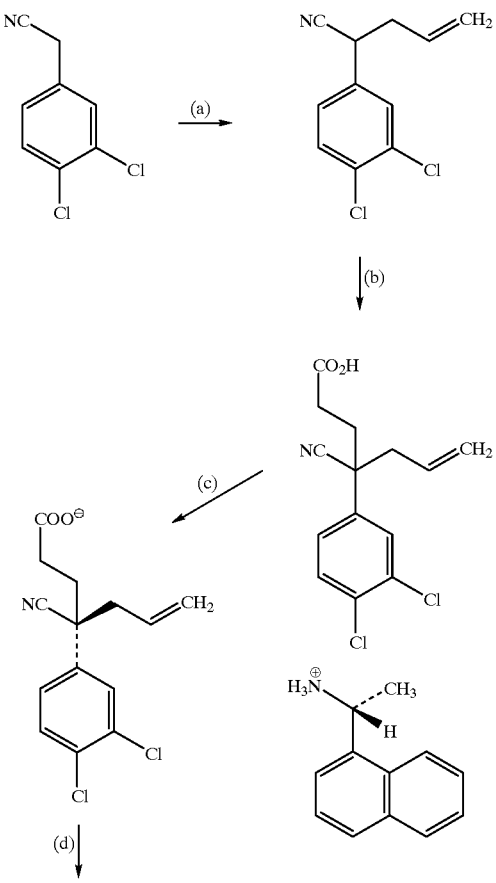

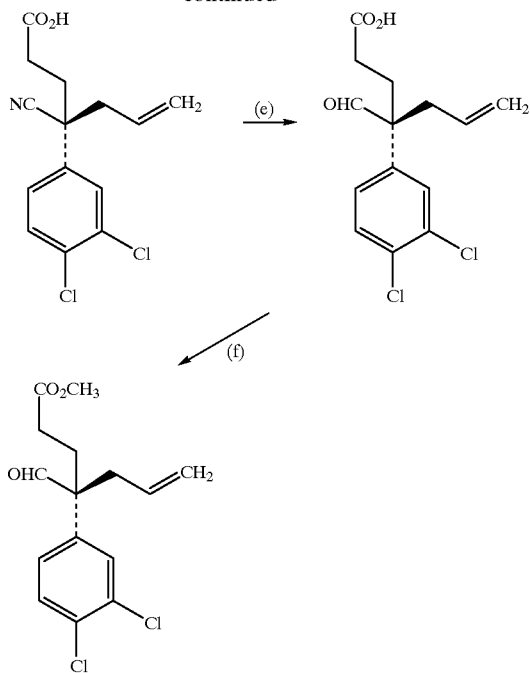

(a) 2-(3,4-Dichlorophenyl)pent 4-enenitrile

To a stirred solution of 3,4-dichlorophenylacetonitrile (800 g, 4.3 mol) in cyclohexane (16 l) at room temperature was carefully added aqueous sodium hydroxide solution (containing 1600 g of sodium hydroxide in 8 l of water). This addition caused an elevation of the reaction temperature to 50° C. Allyl bromide (572 g, 1.1 mol. equiv.) and tetra-n-butylammonium chloride hydrate (40 g, 0.03 mol. equiv.) were then added and the reaction stirred for one hour at 50° C. The aqueous phase was removed and the organic layer washed with water (10 l). The organic phase was filtered through silica gel (1 kg) under reduced pressure to give a yellow filtrate solution. The solvent was removed from the filtrate under reduced pressure to give the title compound as an oil (960 g) of 70% purity which was used without any further purification. TLC Rf=0.71 (silica, diethyl ether:hexane, 1:1, by volume). LRMS m/z=226 (m)$^+$.

$^1$H-NMR (CDCl$_3$): δ=2.6–2.75 (m,2H), 3.85 (t,1H), 5.1–5.25 (m,2H), 5.7–5.9 (m,1H), 7.2–7.25 (m,1H), 7.5–7.55 (m,2H) ppm.

(b) 4-Cyano-4-(3,4-dichlorophenyl)hept-6-enoic acid

To a stirred suspension of 60% w/w sodium hydride/oil dispersion (231 g) in tetrahydrofuran (17 l) under nitrogen at −10° C. was added a solution of 3-bromopropanoic acid (806.5 g) in tetrahydrofuran (6 l), dropwise over three hours. The reaction was allowed to warm to room temperature over 22 hours. The reaction was then cooled to −10° C.

Simultaneously, a solution of the compound of Preparation 4(a) (1633.5 g) in tetrahydrofuran (2.5 l) was added, dropwise over two hours, to a stirred suspension of 60% w/w sodium hydride/oil dispersion (221 g) in tetrahydrofuran (2.5 l) under nitrogen at −10° C. When the addition was complete, this mixture was allowed to warm to room temperature over eighteen hours. This mixture was then cooled to −10° C. and cannulated into the above 3-bromopropanoic acid sodium salt mixture over three hours. The reaction mixture was heated at 50° C. for five hours. The reaction was then cooled, poured into water (8 l) and basified to pH 9.3 using aqueous sodium bicarbonate solution. This mixture was washed with dichloromethane (5×2 l) and the aqueous portion acidified to pH 1.0 using concentrated hydrochloric acid solution. The aqueous solution was extracted with dichloromethane (4×2.5 l) and the organic layers were combined, dried using anhydrous magnesium sulphate, filtered and the filtrate concentrated under reduced pressure to give a yellow oil. This oil was then triturated with hexane (1.5 l) to give the title compound as a cream solid (1155.3 g) which was used directly without any further purification. TLC Rf=0.42 (silica, methanol:dichloromethane, 1:9, by volume). LRMS m/z=316 (m+NH$_4$)$^+$.

$^1$H-NMR (CDCl$_3$): δ=2.15–2.8 (m,6H), 5.1–5.25 (m,2H), 5.55–5.7 (m,1H), 7.2–7.25 (m,1H), 7.5–7.55 (m,2H) ppm.

(c) 4(S)-4-Cyano-4-(3,4-dichlorophenyl)hept-6-enoic acid (R)-(+)-1-(1-naphthyl)ethylamine salt To a solution of the compound of Preparation 4(b) (16 g) in ethyl acetate (50 ml) was added R-(+)-1-(1-naphthyl)ethylamine (4.8 g). The solution was stirred for thirty minutes at room temperature and then the solvent removed under reduced pressure to give a gum. This gum was partially dissolved in hexane:diethyl ether (4:1, by volume, 150 ml) and the sides of the flask scratched to induce crystallisation. The white solid that formed was filtered off and crystallised three times from ethyl acetate to give the title compound (4.9 g). m.p. 153–154° C.

$[α]_{589}^{25}$ −7.1° (c=0.0012).

$^1$H-NMR (CDCl$_3$): δ=1.6 (d,3H), 2.0–2.2 (m,2H), 2.25–2.5 (m,2H), 2.5–2.7 (m,2H), 3.8–4.1 (s,br,3H), 5.0–5.2 (m,3H), 5.5–5.7 (m,1H), 7.15–7.25 (m, 1H), 7.4–7.6 (m,6H), 7.75 (d,1H), 7.9 (d,1H), 8.1 (d,1H) ppm.

(d) 4(S)-4-Cyano-4-(3,4-dichlorophenyl)hept-6-enoic acid

To a stirred solution of the compound of Preparation 4(c) (5.5 g) in dichloromethane (100 ml) was added 1N aqueous hydrochloric acid solution (100 ml). The aqueous layer was then removed and the organic portion washed with 1N aqueous hydrochloric acid solution (70 ml). The organic layer was dried using anhydrous magnesium sulphate, filtered and the filtrate evaporated to dryness under reduced pressure to give the title compound (3.6 g). LRMS m/z=316 (m+NH$_4$)$^+$.

$^1$H-NMR (CDCl$_3$): δ=2.15–2.8 (m,6H), 5.1–5.25 (m,2H), 5.55–5.7 (m,1H), 7.2–7.25 (m,1H), 7.5–7.55 (m,2H) ppm.

(e) 4(S)-4-(3,4-Dichlorophenyl)-4-formylhept-6-enoic acid

To a solution of the compound of Preparation 4(d) (2 g, 6.7 mmol) in toluene (20 ml) at −78° C. under an atmosphere of dry nitrogen was added, dropwise, diisobutylaluminium hydride (8.9 ml of a 1.5 M solution in toluene, 2 mol. equiv.). The mixture was then allowed to warm to −40° C. over three hours. The reaction was cooled to −78° C. and diisobutylaluminium hydride (3 ml of a 1.5 M solution in toluene, 0.66 mol. equiv.) added, dropwise. After one hour a further addition of diisobutylaluminium hydride (1.5 ml of a 1.5 M solution in toluene, 0.33 mol. equiv.) was made and the mixture stirred at −78° C. for one hour.

The reaction mixture was carefully poured into stirred 10% w/w aqueous citric acid solution (60 ml). The mixture was stirred rapidly for 30 minutes. The organic layer was then separated, dried using magnesium sulphate, filtered and the filtrate evaporated to dryness under reduced pressure to provide the title compound which was used directly without further purification.

$^1$H-NMR (CDCl$_3$): δ=2.0–2.5 (m,4H), 2.5–2.9 (m,2H), 5.0–5.3 (m,2H), 5.5–5.7 (m,1H), 7.0–7.5 (m,3H), 4.5 (s,br, 1H) ppm.

(f) Methyl 4(S)-4-(3,4-dichlorophenyl)-4-formylhept-6-enoate

To a solution of the compound of Preparation 4(e) (1.34 g, 4.45 mmol) in dichloromethane (50 ml) under nitrogen at room temperature was added 1-hydroxybenzotriazole hydrate (0.63 g, 1 mol. equiv.) and 1-(3-dimethylaminopropyl)-3-ethylcarbodiimide hydrochloride (1.19 g, 1.4 mol. equiv.). The mixture was stirred for 10 minutes then methanol (0.9 ml, 5 mol. equiv.) was added. The reaction mixture was then stirred at room temperature for three hours.

The solvent was removed by evaporation under reduced pressure and the residue partitioned between ethyl acetate (50 ml) and 0.5 N aqueous hydrochloric acid solution (20 ml). The organic layer was separated, dried using sodium sulphate, filtered and the filtrate evaporated to dryness under reduced pressure to provide the title compound (1.6 g) which was used directly without further purification.

$^1$H-NMR (CDCl$_3$): δ=2.0–3.0 (m,6H), 3.6 (s,3H), 4.9–5.7 (m,3H), 7.0–7.1 (m,1H), 7.2–7.8 (m,2H), 9.5 (s,1H) ppm.

Preparation 5

5(S)-5-Allyl-1-cyclohexyl-5-(3,4-dichlorophenyl)piperidin-2-one

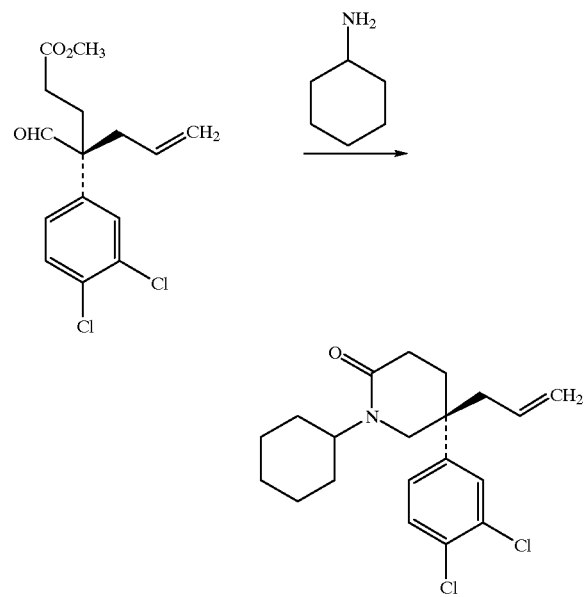

To a solution of the compound of Preparation 4(f) (500 mg, 1.6 mmol) and cyclohexylamine (200 μl, 1.1 mol. equiv.) in tetrahydrofuran (30 ml) at room temperature under nitrogen was added sodium triacetoxyborohydride (470 mg, 1.4 mol. equiv.) and acetic acid (91 μl, 1 mol. equiv.). The reaction was stirred for 18 hours at room temperature and then heated under reflux for four hours. The mixture was then cooled and poured into saturated aqueous sodium carbonate solution (20 ml). The mixture was extracted with ethyl acetate (3×50 ml). The combined organic layers were then dried using sodium sulphate, filtered and the filtrate evaporated to dryness under reduced pressure. The residue was chromatographed using silica gel eluting with methanol:dichloromethane (1:49, by volume). The material obtained by chromatography was taken up in tetrahydrofuran (50 ml) and the solution heated under reflux for 14 hours. The solvent was removed by evaporation under reduced pressure and the residue chromatographed using silica gel eluting with methanol:dichloromethane (1:9, by volume). The material obtained was then rechromatographed using silica gel eluting with a solvent gradient of dichloromethane-:hexane:methanol (9:1:0 changing to 199:0:1, by volume) to provide the title compound as an oil (281 mg). TLC Rf=0.2 (methanol:dichloromethane, 2:98, by volume). LRMS m/z= 366 (m)$^+$.

$^1$H-NMR (CDCl$_3$): δ=1.0–1.2 (m,1H), 1.4–2.5 (m,15H), 3.2–3.3 (m,1H), 3.4–3.5 (m,1H), 4.4–4.6 (m,1H), 5.0–5.2 (m,2H), 5.3–5.5 (m,1H), 7.0–7.1 (m,1H), 7.3–7.5 (m,2H) ppm.

Preparation 6

5(S)-5-Allyl-1-(1-cyclopropylcyclopent-1-yl)-5-(3,4-dichlorophenyl)piperidin-2-one

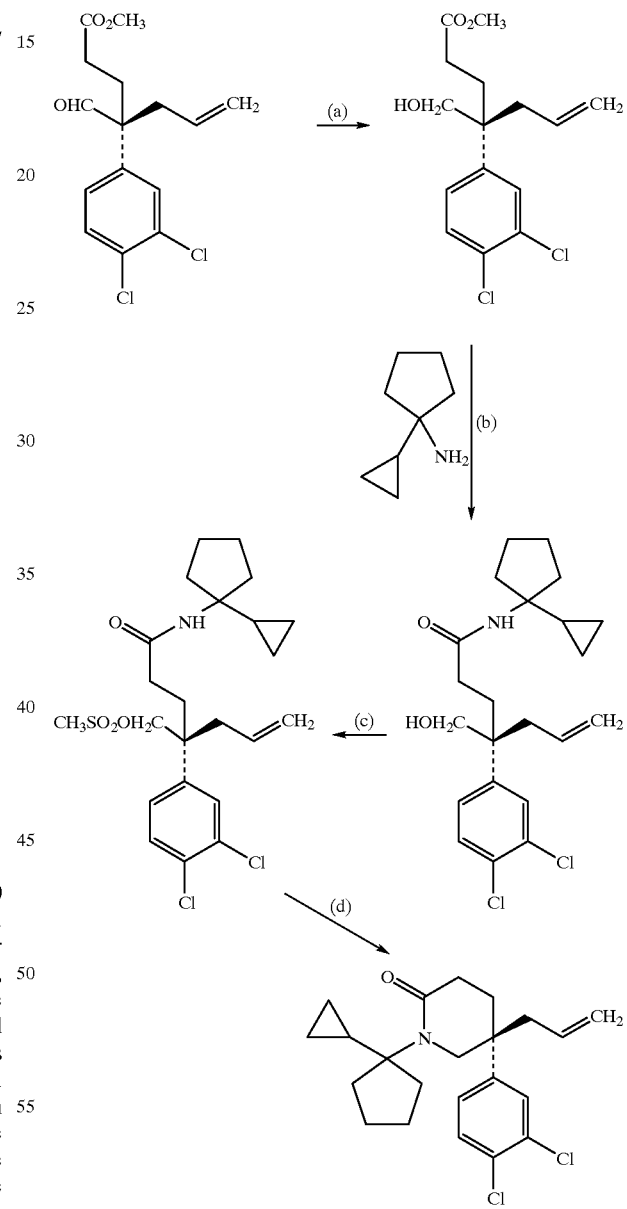

(a) Methyl 4(S)-4-(3,4-dichlorophenyl)-4-hydroxymethylhept-6-enoate

To a solution of the compound of Preparation 4(f) (1.6 g, 5 mmol) in tetrahydrofuran (45 ml) at room temperature under an atmosphere of nitrogen was added sodium triacetoxyborohydride (1.494 g, 1.4 mol. equiv.) and acetic acid (0.29 ml, 1 mol. equiv.). After 5 minutes, triethylamine (1.40 ml, 2 mol. equiv.) was added, and the reaction stirred at room temperature for 18 hours. The solvent was removed by evaporation under reduced pressure and the residue partitioned between saturated aqueous sodium bicarbonate solution (30 ml) and ethyl acetate (30 ml). The organic layer was separated and the aqueous portion extracted with ethyl acetate (2×30 ml). The combined organic layers were dried using sodium sulphate and evaporated to dryness under reduced pressure. The residue was chromatographed on silica gel eluting with ethyl acetate:hexane (1:2, by volume) to give the title compound (307 mg). TLC Rf=0.34 (silica, ethyl acetate:hexane, 1:2, by volume).

(b) N-(1-Cyclopropylcyclopent-1-yl)-4(S)-4-(3,4-dichlorophenyl)-4-hydroxymethylhept-6-enamide A mixture of the compound of Preparation 6(a) (0.73 g, 2.3 mmol) and the compound of Preparation 11 (0.32 g, 1.1 mol. equiv.) was heated at 100° C. in a sealed flask for 16 hours. A further portion of the compound of Preparation 11 (158 mg, 0.55 mol. equiv.) was then added and the mixture again heated in a sealed flask at 100° C. for a further 16 hours. The reaction mixture was cooled and partitioned between ethyl acetate (30 ml) and 1N aqueous hydrochloric acid solution (20 ml). The organic layer was separated, dried using sodium sulphate, filtered and the solvent removed from the filtrate by evaporation under reduced pressure. The residue was chromatographed using silica gel eluting with ethyl acetate:hexane (1:1, by volume) to provide the title compound (0.8 g). LRMS m/z=410 (m)+.

$^1$H-NMR (CDCl$_3$): δ=0.2–0.3 (m,2H), 0.3–0.5 (m,2H), 1.2–1.8 (m,10H), 1.8–2.2 (m,5H), 2.3–2.6 (m,2H), 3.6–3.8 (m,2H), 4.9–5.3 (m,2H), 5.4–5.6 (m,1H), 7.1–7.15 (m,1H), 7.3–7.5 (m,2H) ppm.

(c) N-(1-Cyclopropylcyclopent-1-yl)-4(S)-4-(3,4-dichlorophenyl)-4-methanesulphonyloxymethylhept-6-enamide To a solution of the compound of Preparation 6(b) (0.77 g, 1.88 mmol) in dichloromethane (20 ml) at 0° C. under nitrogen was added triethylamine (0.327 ml, 1.25 mol. equiv.) followed by methanesulphonyl chloride (0.17 ml, 1.2 mol. equiv.). The reaction was stirred for 90 minutes. The solvent was removed by evaporation under reduced pressure and the residue was partitioned between ethyl acetate and aqueous sodium bicarbonate solution. The organic layer was separated, dried using sodium sulphate, filtered and the solvent removed from the filtrate by evaporation under reduced pressure. The resulting oil was chromatographed using silica gel eluting with dichloromethane:methanol (19:1, by volume) to provide the title compound (0.88 g).

$^1$H-NMR (CDCl$_3$): δ=0.2–0.25 (m,2H), 0.3–0.45 (m,2H), 1.2–1.8 (m,8H), 1.8–2.2 (m,6H), 2.4–2.6 (m,2H), 2.95 (s,3H), 4.3–4.4 (m,2H), 5.05–5.3 (m,2H), 5.5–5.65 (m,1H), 7.1–7.2 (m,1H), 7.35–7.5 (m,2H) ppm.

(d) 5(S)-5-Allyl-1-(1-cyclopropylcyclopent-1-yl)-5-(3,4-dichlorophenyl)piperidin-2-one To a solution of the compound of Preparation 6(c) (0.88 g, 1.8 mmol) in tetrahydrofuran (10 ml) was added 60% w/w sodium hydride/oil dispersion (108 mg, 1.5 mol. equiv.). The mixture was stirred for 30 minutes at room temperature under an atmosphere of nitrogen. After this period of time the reaction was heated under reflux for 16 hours. The mixture was then partitioned between a 2% w/w aqueous sodium carbonate solution (40 ml) and ethyl acetate (40 ml). The layers were separated and the aqueous phase was extracted with ethyl acetate (2×30 ml). The combined organic layers were dried using magnesium sulphate, filtered and evaporated to dryness under reduced pressure. The residue was chromatographed using silica gel eluting with dichloromethane:diethyl ether (19:1, by volume) to provide the title compound (0.525 g). TLC Rf=0.15 (silica, ethyl acetate:hexane,1:4, by volume). LRMS m/z=392 (m)+.

$^1$H-NMR (CDCl$_3$): δ=0.3–0.5 (m,4H), 1.4–1.5 (m,1H), 1.5–1.8 (m,4H), 1.8–2.3 (m,7H), 2.3–2.5 (m,2H), 2.5–2.6 (m,1H), 3.4–3.45 (m,1H), 3.6–3.65 (m,1H), 4.9–5.1 (m,2H), 5.3–5.5 (m,1H), 7.15–7.2 (m,1H), 7.35–7.5 (m,2H) ppm.

Preparation 7

5(S)-1-Cyclohexyl-5-(3,4-dichlorophenyl)-5-formylmethylpiperidin-2-one

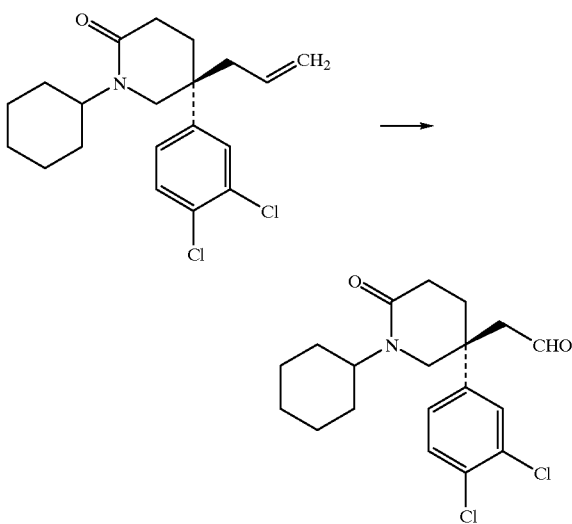

Into a solution of the compound of Preparation 5 (0.358 g, 1 mol. equiv.) in methanol (28 ml) under nitrogen at −78° C. was bubbled ozone at a rate of 50 ml/min. (using a charge of 1.5A to generate the ozone from oxygen) for 15 minutes. After this time the amperage was reduced to zero and oxygen bubbled through the reaction at a rate of 5 ml/min. for two minutes. The oxygen supply was then removed and nitrogen bubbled through the reaction mixture for twenty minutes. After this time, a solution of dimethyl sulphide (0.72 ml, 10 mol. equiv.) in methanol (2 ml) was cautiously added, dropwise, and the reaction left to warm to room temperature over eighteen hours. The solvent was removed under reduced pressure and the reaction mixture was partitioned between ethyl acetate (20 ml) and water (15 ml). The organic layer was separated and the aqueous portion further extracted with ethyl acetate (2×20 ml). The organic layers were then combined, dried using sodium sulphate, filtered and the filtrate evaporated to dryness under reduced pressure to give the title compound (0.361 g) which was used without further purification. TLC Rf=0.31 (silica, methanol:dichloromethane, 1:19, by volume).

$^1$H-NMR (CDCl$_3$): δ=0.2–0.4 (m,2H), 0.5–0.7 (m,2H), 1.0–1.15 (m,1H), 2.0–2.25 (m,2H), 2.3–2.45 (m,1H), 2.6–2.8 (m,1H), 2.9–3.05 (m,1H), 3.1–3.2 (m,1H), 3.4–3.6 (m,2H), 3.9–4.0 (m,1H), 4.05–4.15 (m,1H), 7.15–7.2 (m,1H), 7.3–7.5 (m,2H), 9.5 (s,1H), ppm.

Preparation 8

5(S)-1-(1-Cyclopropylcyclopent-1-yl)-5-(3,4-dichlorophenyl)-5-formylmethylpiperidin-2-one The title compound was prepared by a similar procedure to that described in Preparation 7 using the compound of Preparation 6(d) as the starting material.

Preparation 9

4,4-Difluoro-1-(methanesulphonyloxymethyl) cyclohexane (a) 4,4-Difluorocyclohexylmethanol To a solution of diethylaminosulphur trifluoride (200 ml, 2 mol. equiv.) in dichloromethane (1500 ml) at 0° C. was added a solution of ethyl 4-oxocyclohexanecarboxylate (130 g) in dichloromethane (500 ml), dropwise, over 20 minutes. The mixture was allowed to stir at room temperature overnight. Water (250 ml) was then added carefully (CAUTION: strong exotherm). The mixture was basified with saturated aqueous sodium bicarbonate solution, extracted with dichloromethane and the combined organic layers were washed with saturated aqueous sodium bicarbonate solution, dried over anhydrous magnesium sulphate, filtered and the solvent removed by evaporation under reduced pressure to give an orange/red oil that was distilled under reduced pressure to provide contaminated ethyl 4,4-difluorocyclohexanecarboxylate as a yellow oil (110.7 g), b.p. 60–70° C. at 2 mm Hg.

A portion of this product (1.96 g) was dissolved in dry diethyl ether (15 ml) and added, dropwise, to a stirred suspension of lithium aluminium hydride (350 mg) in dry diethyl ether (30 ml) at 0° C. under nitrogen. The mixture was then allowed to stir for one hour. Water (0.5 ml) was then added followed by 2N aqueous sodium hydroxide solution (0.5 ml) and then water (0.5 ml). The inorganic solids were removed by filtration and the filtrate concentrated by evaporation under reduced pressure to give the contaminated title compound as a colourless oil (1.59 g).

This product was purified on a larger scale by dissolving 5 g of this material in acetone (420 ml) and adding sodium bicarbonate (21 g) and water (105 ml). A solution of OXONE (trade mark) (21 g) in water (105 ml) was then added and the mixture stirred for 1.5 hours. The acetone was removed by evaporation under reduced pressure. 10% w/w Aqueous sodium bicarbonate solution (50 ml) was then added and the mixture extracted with dichloromethane (3×50 ml). The combined organic extracts were then dried over anhydrous sodium sulphate, filtered and concentrated under reduced pressure to provide the purified title compound as a colourless oil (2.4 g).

In a modification of the above procedure, ethyl 4,4-difluorocyclohexanecarboxylate may be prepared from ethyl 4-oxocyclohexanecarboxylate using $SF_4$/HF and dichloromethane as the solvent in an autoclave. With this method, the use of OXONE in the work-up is not necessary. For an alternative preparation of 4,4-difluorocyclohexylmethanol from ethyl 4,4-difluorocyclohexanecarboxylate see Preparation 12.

(b) 4,4-Difluoro-1-(methanesulphonyloxymethyl) cyclohexane

To a solution of the compound of Preparation 9(a) (24.4 g, 162.5 mmol) in dry dichloromethane (800 ml) at 0° C. under an atmosphere of nitrogen was slowly added triethylamine (34 ml, 1.5 mol equiv.) and methanesulphonyl chloride (12.6 ml, 1 mol equiv.) The reaction mixture was stirred for 16 hours at room temperature. Dichloromethane (200 ml) was added and the mixture washed successively with saturated aqueous sodium bicarbonate solution (2×200 ml), 1N aqueous hydrochloric acid solution (2×500 ml) and brine (350 ml). The organic layer was dried over anhydrous sodium sulphate, filtered and evaporated to dryness under reduced pressure to provide a brown oil which crystallised on standing to provide a cream solid (34.7 g). LRMS m/z=246 (m+18)$^+$.

$^1$H-NMR (CDCl$_3$): δ=1.2–1.5 (m,2H), 1.55–1.9 (m,5H), 2.0–2.2 (m,2H), 3.0 (s,3H), 4.0–4.1 (m,2H) ppm.

Caution

It has been noted that the products of Preparations 9(a) and 9(b) are thermally unstable and display autocatalytic decomposition, the onset temperature for which is lowered in the presence of acid. It is therefore recommended that the use of acid is avoided in the work-up and that only basic conditions are used.

Preparation 10

2-Methanesulphonyloxyethylcyclopropane

To a solution of 2-cyclopropylethanol (2.1 g, 24.4 mmol) in dichloromethane (50 ml) at 0° C. under nitrogen was added triethylamine (4.1 ml, 1.2 mol. equiv.). Methanesulphonyl chloride (2.5 ml, 1.3 mol. equiv.) was added, dropwise, and the reaction allowed to stir for 18 hours at room temperature. Water (50 ml) and dichloromethane (50 ml) were added. The organic phase was separated, washed with water (2×50 ml) and then dried over anhydrous sodium sulphate. The solution was filtered and the solvent removed from the filtrate by evaporation under reduced pressure to give the title compound as an oil (4 g). TLC Rf=0.9 (silica, methanol:dichloromethane, 1:19, by volume). LRMS m/z=182 (m+18)$^+$.

$^1$H-NMR (CDCl$_3$): δ=0.1–0.15 (m,2H), 0.5–0.55 (m,2H), 0.7–0.8 (m,1H), 1.6–1.7 (m,2H), 3.00 (s,3H), 4.25–4.3 (m,2H) ppm.

Preparation 11

1-Amino-1-cyclopropylcyclopentane (a) 1-Cyclopropylcyclopentan-1-ol

To a solution of bromocyclopropane (2.54 ml, 31.7 mmol) in diethyl ether (50 ml) at −78° C. under nitrogen was added, dropwise, tert-butyllithium (18.2 ml of a 1.7 M solution in pentane, 31 mmol). Diethyl ether (30 ml) was then added and the mixture stirred for 1 hour at −78° C. A solution of cyclopentanone (2.74 ml, 34 mmol) in diethyl ether (40 ml) was then added dropwise. The reaction was stirred for 4 hours at −78° C. and was then allowed to warm to room temperature over 16 hours. Water (40 ml) was added, cautiously, and the aqueous layer extracted with diethyl ether (2×40 ml). The combined ether layers were dried using sodium sulphate, filtered and evaporated under reduced pressure to give an oily residue. This was chromatographed using silica gel eluting with a solvent gradient of dichloromethane:methanol (100:0 changing to 9:1, by volume) to provide the title compound (3.5 g). TLC Rf=0.4 (silica, dichloromethane:methanol, 9:1, by volume).

$^1$H-NMR (CDCl$_3$): δ=0.3–0.5 (m,4H), 1.05–1.15 (m,2H), 1.5–1.7 (m,6H), 1.7–1.9 (m,2H) ppm.

(b) 1-Amino-1-cyclopropylcyclopentane

To a solution of sodium azide (3.5 g, 54 mmol) in toluene (25 ml) under nitrogen at room temperature was added trifluoroacetic acid (4 ml, 53 mmol). The mixture was cooled to 0° C. and a solution of the compound of Preparation 11(a) (3.35 g, 26.5 mmol) in toluene (5 ml) was added, dropwise. The mixture was stirred for 4 hours and allowed to warm to room temperature. Concentrated ammonium hydroxide solution (25 ml) was then added. The toluene layer was separated and washed with water (2×20 ml). The organic layer was dried using sodium sulphate and filtered. The filtrate was added, dropwise, to a 1M solution of lithium aluminium hydride in tetrahydrofuran (53 ml) at 5° C. under nitrogen. The mixture was stirred at room temperature for sixteen hours and at 50° C. for one hour. Water (1.8 ml) was then added, dropwise, followed by 3N aqueous sodium hydroxide solution (1.8 ml) and water (5.4 ml). The mixture was stirred for 20 minutes filtered and evaporated under reduced pressure to a volume of approximately 20 ml. The solution was washed with 10% w/w aqueous sodium bicarbonate solution (30 ml) and dried using sodium sulphate. The solvent was removed by evaporation under reduced pressure to provide the title compound (2 g) which was used directly without further purification.

$^1$H-NMR (CDCl$_3$): δ=0.15–0.4 (m,4H), 0.8–1.2 (m,3H), 1.3–1.9 (m,8H) ppm.

Preparation 12

4,4-Difluorocyclohexylmethanol

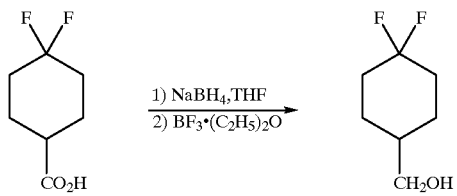

To a slurry of sodium borohydride (74.66 g) in tetrahydrofuran (1500 ml) at 4° C. was added a solution of 4,4-difluorocyclohexanecarboxylic acid (322.6 g) (prepared by conventional hydrolysis of ethyl 4,4-difluorocyclohexanecarboxylate [see Preparation 9(a)] using sodium hydroxide in aqueous ethanol) in tetrahydrofuran (1000 ml) over a 70 minute period maintaining the reaction temperature below 10° C. by external cooling. The slurry was stirred for 1 hour, cooled to 3° C. and boron trifluoride etherate (241 ml) added over 40 minutes maintaining the reaction temperature below 15° C. The reaction was then stirred at room temperature for 18 hours.

95% Aqueous ethanol (1900 ml) was then added over a 5 minute period and this resulted in an initial exotherm causing the reaction temperature to rise from 19 to 23° C. with the rapid evolution of gas. The reaction temperature then dropped to 19° C. during the remainder of the addition. The slurry was stirred for 30 minutes and the solvent removed by evaporation under reduced pressure. The residue was dissolved in a 1:1, by volume, dichloromethane:water (2500 ml) and the layers separated. The aqueous layer was further extracted with dichloromethane (600 ml) and the combined organic layers concentrated under reduced pressure to provide the title compound as an orange oil (281.7 g).

Preparation 13

3-(4-Fluoropiperidin-1-yl)azetidine tosylate

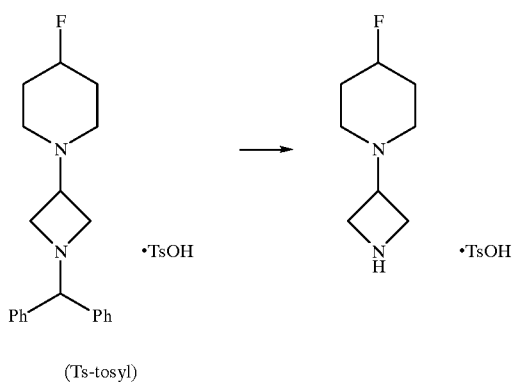

(Ts-tosyl)

A slurry of 3-(4-fluoropiperidin-1-yl)-1-diphenylmethylazetidine tosylate (578 g) (see the modified procedure of Preparation 3(d)) in methanol (8670 ml) was warmed to 45° C. to achieve solution. Fuller's earth (trade mark) (231 g) was added and the green slurry stirred for 2.5 hours at about 50° C. The mixture was filtered and the filtrate stirred overnight at room temperature. The yellowish slurry was heated to 55° C., activated carbon (NORIT A, trade mark) (289 g) was added and the mixture heated under reflux for 1 hour. The mixture was cooled and filtered through a filter aid (ARBACEL, trade mark), 10% w/w palladium/carbon (containing 50% by weight of water) (231 g) and ammonium formate (283.4 g) were added to the filtrate and the mixture heated under reflux for 2.5 hours.

Further 10% w/w palladium/carbon (containing 50% by weight of water) (115 g) was added and the heating under reflux continued for 1 hour. The reaction mixture was cooled, filtered through a filter aid (ARBACEL, trade mark) and the filtrate concentrated under reduced pressure to give an oily white solid that was allowed to stand for 48 hours. This solid was then granulated in ethyl acetate (3000 ml) for 30 minutes and the resulting white solid filtered off and dried to provide the title compound as a white solid (282.7 g). $^1$H-NMR analysis showed the molar ratio of free base:para-toluenesulphonic acid to be 1:1.15–1.35.

Preparation 14

5(S)-5-(3,4-Dichlorophenyl)-1-(4,4-difluorocyclohexylmethyl)-5-(2,2-dimethoxyethyl) piperidin-2-one

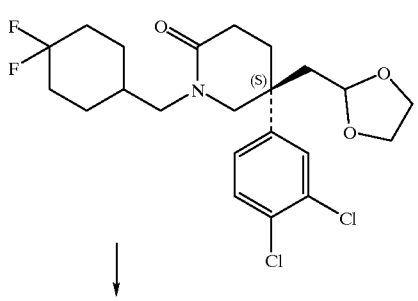

37

-continued

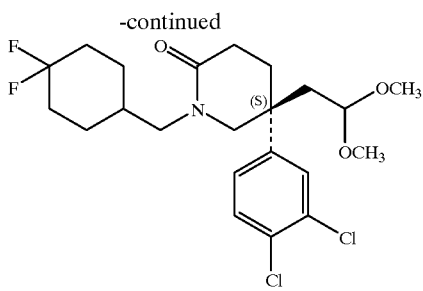

To a solution of the compound of Preparation 1(c) (238 g) in methanol (2400 ml) was added Amberlyst 15 (trade mark) ion exchange resin (120 g) and the slurry stirred at room temperature for 24 hours. The mixture was filtered, the filtrate concentrated under reduced pressure and the residual yellow gum taken up in dichloromethane (2000 ml) and washed with water (3×2000 ml). The organic layer was concentrated under reduced pressure and the residue taken up in methyl t-butyl ether (500 ml). The mixture was concentrated under reduced pressure to a volume of about 250 ml and the slurry then stirred for 2 hours. The resulting white solid was filtered off and dried to provide the title compound (180.66 g).

Preparation 15

5(S)-5-(3,4-Dichlorophenyl)-1-(4,4-difluorocyclohexylmethyl)-5-formylmethylpiperidin-2-one

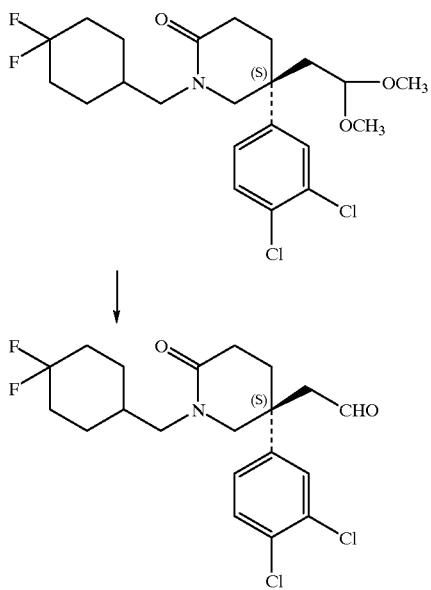

To a stirred solution of the compound of Preparation 14 (179.25 g) in tetrahydrofuran (900 ml) was added 1N aqueous hydrochloric acid solution (900 ml). The mixture was stirred at room temperature for 24 hours and then the organic solvent removed under reduced pressure. The aqueous residue was extracted with dichloromethane (3×600 ml), the organic layers combined and the solvent removed under reduced pressure to give a white solid (163.8 g). This material was slurried in methyl isobutyl ketone (250 ml) for 1 hour. The solid obtained was filtered off and dried to provide the title compound (145.15 g).

38

Pharmacological Data

The affinity of a selection of the compounds of the preceding Examples for the human $NK_2$ receptor was tested in vitro by testing their ability to compete with [$^3$H] NKA for binding to membranes prepared from Chinese hamster ovary cells expressing the cloned human $NK_2$ receptor using the method set out on page 26.

The results obtained are tabulated below.

| Example no. | pKi |
|---|---|
| 1 | 9.2 |
| 2 | 10.3 |
| 3 | 10.0 |
| 4 | 8.6 |

The "pKi" measurement is the negative logarithm of the molar affinity of the compound for the receptor as determined in radioligand binding assays using standard protocols.

What is claimed is:

1. A compound of the formula:

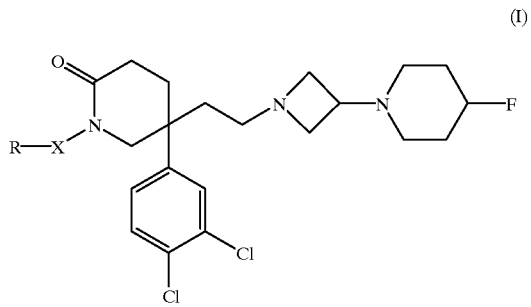

(I)

or a pharmaceutically acceptable acid addition salt thereof,
wherein X is a direct link or $C_1$–$C_4$ alkylene; and
R is $C_3$–$C_7$ cycloalkyl optionally substituted by 1 or 2 substituents each independently selected from fluoro and $C_3$–$C_7$ cycloalkyl:
with the proviso that X is not methylene when R is cyclopropyl.

2. A compound as claimed in claim 1 wherein X is a direct link, methylene or ethylene.

3. A compound as claimed in claim 1 wherein X is methylene.

4. A compound as claimed in claim 1 wherein R is $C_3$–$C_6$ cycloalkyl optionally substituted by 1 or 2 substituents each independently selected from fluoro and cyclopropyl.

5. A compound as claimed in claim 1 wherein R is cyclopropyl, 1-cyclopropylcyclopent-1-yl, cyclohexyl or 4,4-difluorocyclohexyl.

6. A compound as claimed in claim 1 wherein R is 4,4-difluorocyclohexyl.

7. A compound as claimed in claim 1 wherein R is 4,4-difluorocyclohexyl and X is methylene; R is cyclohexyl and X is a direct bond; R is 1-cyclopropylcyclopent-1-yl and X is a direct bond; or R is 2-cyclopropyl and X is ethylene.

8. A compound having the formula:

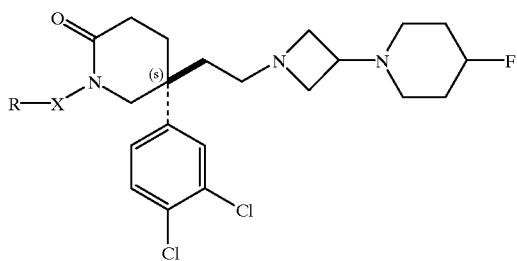

(IA)

or a pharmaceutically acceptable acid addition salt thereof,
wherein X is a direct link or $C_1-C_4$ alkylene; and R is $C_3-C_7$ cycloalkyl optionally substituted by 1 or 2 substituents each independently selected from fluoro and $C_3-C_7$ cycloalkyl; with the proviso that X is not methylene when R is cyclopropyl.

9. 5(S)-5-(3,4-Dichlorophenyl)-1-(4,4-difluorocyclohexylmethyl)-5-(2-[3-(4-fluoropiperidin-1-yl)]azetidin-1-yl)ethylpiperidin-2-one or an acid addition salt thereof.

10. 5(S)-5-(3,4-Dichlorophenyl)-1-(4,4-difluorocyclohexylmethyl)-5-(2-[3-(4-fluoropiperidin-1-yl)]azetidin-1-yl)ethylpiperidin-2-one disuccinate.

11. A pharmaceutical composition comprising a compound of the formula (I), or a pharmaceutically acceptable acid addition salt thereof, as claimed in claim 1, together with a pharmaceutically acceptable diluent or carrier.

12. A compound of claim 8 wherein X is a direct link, methylene or ethylene.

13. A compound of claim 8 wherein X is methylene.

14. A compound of claim 8 wherein R is $C_3-C_6$ cycloalkyl optionally substituted by 1 or 2 substituents each independently selected from fluoro and cyclopropyl.

15. A compound of claim 8 wherein R is cyclopropyl, 1-cyclopropylcyclopent-1-yl, cyclohexyl or 4,4-difluorocyclohexyl.

16. A compound of claim 8 wherein R is 4,4-difluorocyclohexyl.

17. A compound of claim 8 wherein R is 4,4-difluorocyclohexyl and X is methylene; R is cyclohexyl and X is a direct bond; R is 1-cyclopropylcyclopent-1-yl and X is a direct bond; or R is 2-cyclopropyl and X is ethylene.

* * * * *